(12) United States Patent
Jedlina

(10) Patent No.: US 11,110,115 B2
(45) Date of Patent: Sep. 7, 2021

(54) NUCLEIC ACID MOLECULE WITH ANTI-INFLAMMATORY AND ANTI-COAGULANT AND ORGAN-PROTECTIVE PROPERTIES

(71) Applicant: APTAHEM AB, Malmo (SE)

(72) Inventor: Luiza Anna Jedlina, Malmo (SE)

(73) Assignee: APTAHEM AB, Malmö (SE)

( * ) Notice: Subject to any disclaimer, the term of this patent is extended or adjusted under 35 U.S.C. 154(b) by 13 days.

(21) Appl. No.: 16/652,926

(22) PCT Filed: Oct. 3, 2018

(86) PCT No.: PCT/EP2018/076912
§ 371 (c)(1),
(2) Date: Apr. 1, 2020

(87) PCT Pub. No.: WO2019/068766
PCT Pub. Date: Apr. 11, 2019

(65) Prior Publication Data
US 2020/0268784 A1 Aug. 27, 2020

(30) Foreign Application Priority Data

Oct. 3, 2017 (EP) .................................. 17194536
May 8, 2018 (EP) .................................. 18171219

(51) Int. Cl.
| | |
|---|---|
| *A61K 31/7105* | (2006.01) |
| *C12N 15/115* | (2010.01) |
| *A61P 7/02* | (2006.01) |
| *A61K 31/7115* | (2006.01) |
| *A61K 9/00* | (2006.01) |

(52) U.S. Cl.
CPC ...... *A61K 31/7105* (2013.01); *A61K 31/7115* (2013.01); *A61P 7/02* (2018.01); *C12N 15/115* (2013.01); *A61K 9/0019* (2013.01)

(58) Field of Classification Search
None
See application file for complete search history.

(56) References Cited

FOREIGN PATENT DOCUMENTS

WO   2009/099378 A1   8/2009

OTHER PUBLICATIONS

International Search Report of PCT/EP2018/076912 dated Jan. 2, 2019.
Written Opinion of PCT/EP2018/076912 dated Jan. 2, 2019.
Burrell, K., et al., "A Kallikrein-Targeting RNA Aptamer Inhibits the Intrinsic Pathway of Coagulation and Reduces Bradykinin Release," Journal of Thrombosis and Haemostasis, vol. 15, No. 9, pp. 1807-1817 (Aug. 2, 2017).
Francischetti, I., et al., "Defibrotide Interferes With Several Steps of the Coagulation-Inflammation Cycle and Exhibits Therapeutic Potential to Treat Severe Malaria," Arteriosclerosis, Thrombosis, and Vascular Biology, vol. 32, No. 3, pp. 786-698 (Nov. 23, 2011).
Woodruff, R., et al., "Modulation of the Coagulation Cascade Using Aptamers," Arteriosclerosis, Thrombosis, and Vascular Biology, vol. 35, No. 10, pp. 2083-2091 (Aug. 27, 2015).

*Primary Examiner* — Sean Mcgarry
(74) *Attorney, Agent, or Firm* — Polsinelli PC; Tara A. Nealey

(57) ABSTRACT

The invention relates to a nucleic acid molecule or a composition comprising said molecule for use as an anti-inflammatory and/or anti-coagulant and/or organ-protective medicament. The invention also relates to a use of said nucleic acid molecule or said composition, for the manufacture of a medicament for preventing, treating, regressing, curing and/or delaying a disease or a condition wherein inflammation and/or coagulation and/or organ damage or failure occurs in an individual. Finally, the invention further relates to a method for alleviating one or more symptom(s) and/or characteristic(s) and/or for improving a parameter of a disease or condition wherein inflammation and/or coagulation and/or organ damage or failure occur in an individual, the method comprising administering to said individual said nucleic acid molecule or said composition.

17 Claims, 9 Drawing Sheets

Specification includes a Sequence Listing.

A

B

C

A

B

A

| Group | Median survival (hours) | p value | Survival incidence | p value |
|---|---|---|---|---|
| Vehicle | 43.0 | | 1/10 | |
| SEQ ID NO:2  10 mg/kg | 61.0 | 0.1378 | 4/10 | 0.1116 |
| SEQ ID NO:2  25 mg/kg | >73.0# | 0.0382 | 6/10 | 0.0148 |
| SEQ ID NO:2  50 mg/kg | >73.0# | 0.0610 | 7/10 | 0.0042 |
| SEQ ID NO:2  100 mg/kg | >73.0# | 0.0243 | 8/10 | 0.0009 |
| SEQ ID NO:2 50 mg/kg (60 min + 120 min) | >73.0# | 0.1445 | 6/10 | 0.0148 |

$p<0.05$ vs. respective vehicle
$p<0.10$ vs. respective vehicle

B

NUCLEIC ACID MOLECULE WITH ANTI-INFLAMMATORY AND ANTI-COAGULANT AND ORGAN-PROTECTIVE PROPERTIES

CROSS REFERENCE TO RELATED APPLICATIONS

The present application is the 35 U.S.C. 371 National Stage of International Application Number PCT/EP2018/076912, filed Oct. 3, 2018, which claims priority from European patent application 17194536.3, filed Oct. 3, 2017 and European patent application 18171219.1, filed May 8, 2018, the contents of each of which are incorporated herein by reference.

SEQUENCE LISTING SUBMISSION VIA EFS-WEB

A computer readable text file, entitled "031902-5030-US-Amended-Sequence-Listing.txt", created on or about Apr. 24, 2020, with a file size of about 4000 bytes contains the sequence listing for this application and is hereby incorporated by reference in its entirety.

FIELD OF THE INVENTION

The invention relates to a nucleic acid molecule or a composition comprising said molecule for use as an anti-inflammatory and/or anti-coagulant and/or organ-protective medicament. The invention also relates to a use of said nucleic acid molecule or said composition, for the manufacture of a medicament for preventing, treating, regressing, curing and/or delaying a disease or a condition wherein inflammation and/or coagulation and/or organ damage or failure occur in an individual. Finally, the invention further relates to a method for alleviating one or more symptom(s) and/or characteristic(s) and/or for improving a parameter of a disease or condition wherein inflammation and/or coagulation and/or organ damage or failure occur in an individual, the method comprising administering to said individual said nucleic acid molecule or said composition.

BACKGROUND OF THE INVENTION

Disseminated intravascular coagulation (DIC) is characterized by the systemic activation of coagulation caused by various underlying diseases, with sepsis being the leading cause (Gando S et al 2008).

Sepsis and DIC is a common, serious and acute diseases condition that occurs when excessive host immune responses are induced by infectious organisms, cancer, surgery or trauma and is a leading cause of death in hospitalized patients (Clowes G. H. et al 1970, Parrillo J. E. et al, 1990 and Lei M. G. et al, 2003). As a defense mechanism, the immune system initiates a rapid increase of pro-inflammatory and pro-thrombotic mediators leading to lethal systemic tissue damage and multiple organ failure or multiple organ dysfunction syndrome.

Today, the health care system lacks of effective treatment to reduce the risk of organ damage or failure until the infection is under control, and the clinical need is high.

At present, enormous efforts are taken to unravel the molecular mechanisms that lead to changes in inflammation and coagulation.

There is currently no effective known medicament that may be used for specifically preventing, treating, regressing, curing and/or delaying a disease or a condition wherein inflammation and/or coagulation and/or organ damage or failure occurs.

Therefore, there is still a need for new treatments of disease or conditions associated with inflammation and/or coagulation and/or organ damage or failure.

DESCRIPTION OF THE INVENTION

Surprisingly, it has been found that a nucleic acid molecule as defined herein exhibits unexpected anti-inflammatory, anti-coagulant and organ-protective properties.

In a first aspect of the invention, there is provided a nucleic acid molecule for use as an anti-inflammatory and/or anti-coagulant and/or organ-protective medicament wherein said nucleic acid molecule is represented by a nucleotide sequence that has at least 95% sequence identity with a nucleotide sequence comprising SEQ ID NO:1 or SEQ ID NO:2.

SEQ ID NO:1 is the following nucleic acid sequence:

```
5' GGG AAUUCG AGC UCG GUA CCA ACA AUA CGA CUA CAC
CAU CAA AAG UAU UAU CUU GCA UCG AAG GUU GGC ACG
UAG CAA GCU CUG CAG UCG 3'
```

SEQ ID NO:2 is the following nucleic acid sequence:

```
5' GGG AAU^F U^FC^FG AGC^F U^FC^FG GU^FA C^FC^FA AC^FA AU^FA
C^FGA C^FU^FA C^FAC^F C^FAU^F C^FAA AAG U^FAU^F U^FAU^F C^FU^FU^F
GC^FA U^FC^FG AAG GU^FU^F GGC^F AC^FG U^FAG C^FAA GC^FU^F
C^FU^FG C^FAG U^FC^FG 3'
```

Each C and U of SEQ ID NO:2 is fluorinated (i.e. $U^F$, $C^F$) to increase stability of the molecule in plasma.

In the context of the invention, a nucleic acid molecule may be a synthetic or natural or recombinant or modified molecule compared to SEQ ID NO:1 as identified above in the sense that:

One, 2, 3, 4 or 5 or at least 20%, 30%, 40%, 50%, 60%, 70%, 80%, or at least 90% or 100% of their nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of their nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

In the context of the invention, a nucleic acid molecule may be a modified molecule compared to SEQ ID NO:2 as identified above in the sense that:

One, 2, 3, 4 or 5 or at least 20%, 30%, 40%, 50%, 60%, 70%, 80%, or at least 90% or 100% of their nucleotides has been deleted or added compared to the corresponding nucleotide present in the naturally occurring molecule, and/or One, 2, 3, 4 or 5 or at least 20%, 30%, 40%, 50%, 60%, 70%, 80%, or at least 90% or 100% of their nucleotides, nucleosides, nucleobases, nucleobases linker moiety, and/or backbone moiety has been replaced or substituted by a corresponding nucleotide, nucleoside, nucleobase, nucleobase linker moiety and/or backbone moiety not occurring in the naturally occurring molecule.

Preferably the nucleic acid molecule is represented by a sequence comprising or consisting of SEQ ID NO:1 or 2. A preferred nucleic acid molecule is a nucleic acid molecule comprising SEQ ID NO:1 or 2 and having a length of 1, 2, 3, 4, 5, 6, 7, 8, 9 or 10 nucleotides more than SEQ ID NO:1 or 2.

The chemical structure of the nucleotides of a nucleic acid molecule may be modified, replaced, substituted compared to the structure of a RNA molecule to increase stability, binding affinity and/or specificity. Said nucleic acid molecule may comprise or consist of a RNA molecule or preferably a modified RNA molecule. A preferred modified RNA molecule comprises a modified sugar. One example of such modification is the introduction of a 2'-O-methyl or a 2'-O-methoxyethyl group or an halogen (i.e. fluoro, chloro, bromo or iodo) group on the nucleic acid to improve nuclease resistance and binding affinity to RNA. A preferred halogen group in this context is fluoro as in SEQ ID NO:2. Another example of such modification is the introduction of a methylene bridge connecting the 2'-O atom and the 4'-C atom of the nucleic acid to lock the conformation (Locked Nucleic Acid (LNA)) to improve affinity towards complementary single-stranded RNA. A third example is the introduction of a phosphorothioate group as linker between nucleic acid in the RNA-strand to improve stability against a nuclease attack. The binding affinity of the nucleic acid molecule may be further modified to refine its binding properties as described in Hasegawa H et al., incorporated herein by reference. More detailed information is provided as to other chemical modifications in the general part dedicated to the definitions.

Accordingly a preferred nucleic acid molecule for use as defined herein is a nucleic acid molecule which is single stranded and/or wherein a nucleotide of this nucleic acid molecule is modified compared to a nucleotide present in RNA.

According to a more preferred embodiment, said nucleic acid molecule for use is such that one of its pyrimidines is fluorinated and preferably all its pyrimidines are fluorinated as is in SEQ ID NO:2.

Identity may be at least 95%, 96%, 97%, 98%, 99% or 100%. Identity is preferably assessed on the whole SEQ ID NO as identified herein. However, identity may also be assessed on part of a given SEQ ID NO. Part may mean at least 50% of the length of the SEQ ID NO, at least 60%, at least 70%, at least 80%, at least 90% or 100%. More detailed information is provided as to identity assessment in the general part dedicated to the definitions.

A nucleic acid molecule of the invention is preferably for use as an anti-inflammatory and/or anti-coagulant and/or organ-protective medicament since it exhibits anti-inflammatory and/or anti-coagulation and/or organ-protective properties or characteristics as explained below and as demonstrated in the experimental part.

In an embodiment, a nucleic acid molecule of the invention is for use as an anti-inflammatory and/or anti-coagulant and/or organ-protective medicament since it exhibits anti-inflammatory and/or anti-coagulation and/or organ-protective properties or characteristics as explained below and as demonstrated in the experimental part.

In an embodiment, a preferred activity of a nucleic acid molecule of the invention is to induce a detectable anti-inflammatory activity (i.e. decrease of an inflammatory activity and/or increase of an anti-inflammatory activity). Any compound or any parameter known to be associated with increased or decreased inflammation may be used as read out for assessing the activity of the nucleic acid molecule of the invention.

An anti-inflammatory activity may be assessed by the detection of an increase of the expression level of an anti-inflammatory cytokine and/or the decrease of the expression level of a pro-inflammatory cytokine. Examples of pro-inflammatory cytokines are IL1beta, IL-6, TNFalpha and HMGB1. An example of an anti-inflammatory cytokine is IL-10.

Another parameter linked to inflammation is the detection of inflammatory infiltrates of leukocytes.

Another parameter linked to inflammation is the detection of the expression of pro-inflammatory receptor MAC-1 (CD11b/CD18) or P-selectin or CD36 or EPCR (endothelial protein C receptor).

Another parameter linked to inflammation is the detection of the expression of L-selectin, CD35, CD88, ICAM-1 (intercellular adhesion molecule 1) or PECAM-1 (platelet endothelial cell adhesion molecule 1).

Another parameter linked to inflammation is the detection of fibrinogen, which is a positive acute-phase protein.

Within the context of the invention a parameter linked with inflammation is selected from the group consisting of: increase of the expression level of an anti-inflammatory cytokine, decrease of the expression level of a pro-inflammatory cytokine, IL1beta, IL-6, TNFalpha, HMGB1, IL10, inflammatory infiltrates of leukocytes, MAC-1, P-selectin, CD36, EPCR, CD35, CD88, ICAM-1, PECAM-1 and fibrinogen.

In another embodiment, another preferred activity of a nucleic acid molecule of the invention is to induce a detectable anti-coagulation activity. Any compound or any parameter known to be associated with increased or decreased coagulation may be used as read out for assessing the activity of the nucleic acid molecule of the invention.

A preferred parameter linked with coagulation and used in this context is APTT (Activated Partial Thromboplastin Time), fibrin clot density, thrombin formation, bleeding time, D-dimers, fibrinolytic activity (tPA (tissue plasminogen activator), complex between PAI-1 (plasminogen activator inhibitor-1) and tPA), expression of anti-coagulant protein-S and/or EPCR. Another parameter linked with coagulation and used in this context is fibrinogen (Factor I), heparan sulfate or expression of thrombomodulin, PECAM-1 or protein C. Low levels of fibrinogen are often related to consumption of fibrinogen such as may be seen with disseminated intravascular coagulation (DIC) and abnormal fibrinolysis.

Within the context of the invention a parameter linked with coagulation is selected from the group consisting of: APTT, fibrin clot density, thrombin formation, bleeding time, D-dimers, fibrinolytic activity (tPA, complex between PAI-1 and tPA), expression of anti-coagulant protein-S, expression of EPCR, fibrinogen, heparan sulfate, expression of thrombomodulin, expression of PECAM-1 and expression of protein C.

In another embodiment, another preferred activity of a nucleic acid molecule of the invention is to induce a detectable organ-protective activity, preferably for kidney and/or liver damage or failure. Any compound or any parameter known to be associated with increased or decreased organ damage or failure, preferably kidney and/or liver damage or failure, may be used as read out for assessing the activity of the nucleic acid molecule of the invention.

A preferred parameter linked with organ damage or failure and used in this context is the serum level of AST (aspartate aminotransferase), ALT (alanine aminotransferase), GGT (gamma-glutamyl transpeptidase), ALP (alkaline phosphatase), LDH (lactate dehydrogenase), creatine kinase, BUN (blood urea nitrogen), albumin, creatinine, glucose, bile acid, total bilirubin, conjugated bilirubin, phosphorus, total protein, LDL cholesterol, HDL cholesterol, cholesterol and/or triglycerides.

A preferred parameter linked with liver damage or failure is AST, ALT, GGT, ALP, LDH, albumin, bile acid total bilirubin, conjugated bilirubin, and/or phosphorus.

A preferred parameter linked with kidney damage or failure is creatinine, BUN and/or phosphorus.

Such activity, parameter as defined herein may be assessed in an individual, in an animal model, in a cell, preferably of an animal model or of an individual. The assessment of the activity may be carried out using techniques known to the skilled person. Examples of assays are provided in the experimental part.

The assessment of the expression of a pro-inflammatory or of an anti-inflammatory cytokine may be carried out at the mRNA level, preferably using RT-qPCR. The assessment of expression of said cytokine may be carried out at the protein level, preferably using assays detecting protein expression, such as Western blot analysis, ELISA, flow cytometry, immunohistochemistry or immunofluorescence analysis of cross-sections and/or using an assay as defined later herein. The detection of inflammatory infiltrates of leukocytes or of pro-inflammatory receptor MAC-1 or P-selectin or of CD36 or of EPCR may be carried out using immunofluorescence. The detection of L-selectin, CD35, CD88, ICAM-1 or PECAM-1 may be carried out using immunofluorescence.

The assessment of APTT, fibrin clot density, thrombin formation, bleeding time, fibrinolytic activity (tPA, complex between PAI-1 and tPA), expression of anti-coagulant protein-S and/or EPCR is done using techniques known to the skilled person, preferably as done in the experimental part. The assessment of fibrinogen, heparan sulfate, expression of thrombomodulin, PECAM-1 and/or protein C is done using techniques known to the skilled person, preferably as done in the experimental part.

The assessment of the serum level of AST, ALT, GGT, ALP, LDH, creatine kinase, BUN, albumin, creatinine, glucose, bile acid, total bilirubin, conjugated bilirubin, phosphorus, total protein, LDL cholesterol, HDL cholesterol, cholesterol and/or triglycerides is done using techniques known to the skilled person, preferably as done in the experimental part. The assessment is preferably carried out at several time points for a given subject or at one or several time points for a given subject and a healthy control. The assessment may be carried out each week, each month.

The detection of the presence of a nucleic acid molecule of the invention may be carried out using any technique known to the skilled person. The assessment of the expression level or of the presence of said molecule is preferably performed using classical molecular biology techniques such as (real time) qPCR, microarrays, bead arrays, RNAse protection analysis or Northern analysis. The skilled person will understand that alternatively or in combination with the quantification of said molecule, the quantification of a substrate of a corresponding molecule or of any compound known to be associated with a function of said molecule or the quantification of a function or activity of said molecule using a specific assay is encompassed within the scope of the invention.

A nucleic acid molecule as defined herein may be used as such as a naked molecule, with or without chemical modifications, or present or formulated in a composition or conjugated to a moiety. Accordingly, in a further aspect, there is provided a composition comprising a nucleic acid molecule as defined herein which is for use as defined herein, wherein the composition is preferably a pharmaceutical composition said pharmaceutical composition comprising a pharmaceutically acceptable carrier, adjuvant, salt, diluent and/or excipient. A preferred composition comprises said molecule encapsulated into a particle, preferably a nanoparticle or a liposomal structure. Additional compositions are disclosed in the general part dedicated to the definitions.

In a preferred embodiment, a nucleic acid molecule or a composition for use as defined herein is for intravenous, orally, subcutaneous or intramuscular administration. If inflammation is to be combated, oral or intramuscular administration is preferred. If coagulation is to be combated, intravenous administration is preferred. Very good results were obtained for an anti-coagulation effect using intravenous administration. If both are to be combated, oral, intramuscular and/or intravenous administration are preferred.

In the context of the invention, any disease or condition wherein inflammation and/or coagulation and/or organ damage or failure is involved or is associated or occurs may be prevented, delayed, cured, regressed and/or treated with a nucleic acid molecule or a composition comprising said molecule as defined herein. In a disease or condition as defined herein, inflammation and/or coagulation and/or organ damage or failure may be detectable during the development of said disease or condition, i.e. after the apparition of a symptom of said disease or condition. Alternatively, inflammation and/or coagulation and/or organ damage or failure may be detectable before the development of said disease or condition.

In an embodiment, the disease or condition wherein inflammation occurs is selected from rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, non-alcoholic steatosis, sarcoidosis, autoimmune diabetes, diabetes mellitus, uveitis, multiple sclerosis, Controlling Allograft Rejection after organ transplantation, graft versus host disease (GVHD), inflammatory lung diseases including asthma and chronic obstructive pulmonary disease (COPD), systemic lupus erythematosus (SLE), sarcoidosis, atopic dermatitis and cancer, or a complication or an effect of the progression that is linked to one of these diseases or conditions.

In another embodiment, the disease or condition wherein coagulation occurs is selected from acute coronary syndrome (ACS), thrombosis, peripheral vessel obstruction, obstructive arteriosclerosis, vasculitis, functional disorder occurring after heart surgery, complication caused by organ transplantation, angina pectoris, transient ischemic attack, toxemia of pregnancy (preeclampsia, eclampsia), diabetes, liver veno-occlusive disease (VOD), deep venous thrombosis (DVT), sepsis, septic shock, severe sepsis, trauma, acute respiratory distress syndrome (ARDS) and disseminated intravascular coagulation (DIC), or a complication or an effect of the progression that is linked to one of these diseases or conditions.

In another embodiment, the disease or condition wherein organ damage or failure occurs is selected from infection, poisoning, aspiration syndromes, hypoperfusion or shock, heat-induced illness, ischemia, ischemia-reperfusion injury (IRI), autoimmune disease, trauma, hemorrhage, pancreatitis, bacteremia, burns, sepsis, septic shock, severe sepsis, acute respiratory distress syndrome (ARDS), toxemia of pregnancy (preeclampsia), eclampsia, systemic inflammatory response syndrome (SIRS), disseminated intravascular coagulation (DIC) and multiple organ failure or multiple organ dysfunction syndrome, or a complication or an effect of the progression that is linked to one of these diseases or conditions. Organ damage or failure is preferably liver damage or failure, kidney damage or failure.

There is currently no effective known medicament that may be used for specifically preventing, treating, regressing, curing and/or delaying a disease or condition associated with inflammation and/or coagulation and/or organ damage or failure.

The invention includes increasing an activity or the steady-state level or the expression level or the amount of a nucleic acid molecule or a composition comprising said molecule as defined herein. An activity or a steady-state level of said nucleic acid molecule is increased in a subject, in a cell of said subject, in a tissue of said subject or in body fluid of said subject.

An activity or steady-state level or expression level or amount of said at least one nucleic acid molecule is increased in order to induce a detectable anti-inflammatory and/or anti-coagulation and/or organ-protective activity in a subject, preferably in cells from said subject.

The assessment of the expression level of a nucleic acid molecule as defined herein is preferably carried out in a biopsy or section at several time points for a given subject or at one or several time points for a given subject and a healthy control. The assessment may be carried out at regular time intervals, e.g. each week, each month. The increase/decrease may therefore be assessed regularly, e.g. each week, each month. A detectable decrease of inflammation and/or a detectable decrease of coagulation and/or a detectable decrease of organ damage or failure is preferably assessed as later explained herein to define an anti-inflammatory effect and/or an anti-coagulation effect and/or an organ-protective effect.

An activity or steady-state level or expression level of said nucleic acid molecule may be increased at the level of the molecule itself, e.g. by providing said molecule to a subject, preferably to a cell of a subject, or to a tissue of said subject, or to an organ of said subject or to said subject said molecule being from an exogenous source. For provision of a molecule from an exogenous source, said molecule may conveniently be produced by expression of a nucleic acid encoding said molecule or encoding a source of said molecule thereof in a suitable host cell as described below or as completely synthetic molecules by chemical synthesis.

An activity or steady-state level or expression level of said nucleic acid molecule is increased by regulating the expression level of a nucleotide sequence encoding said molecule. Preferably, the expression level of a nucleic acid molecule is regulated in a cell of said subject or in a tissue of said subject or in the subject. The expression level of said nucleic acid molecule may be increased by introduction of said molecule or an expression construct (or vector) into a cell, tissue, organ or body fluid of said subject, or in the subject whereby an expression vector comprises a nucleotide sequence comprising said molecule, and whereby a nucleotide sequence is under control of a promoter capable of driving expression of a nucleotide sequence in said cell, tissue, organ, subject. The expression level of said molecule may also be increased by introduction of an expression construct into a cell, tissue, organ, subject, whereby a construct comprises a nucleotide sequence encoding a factor capable of trans-activation of an endogenous nucleotide sequence encoding said molecule.

An activity or steady-state level or amount of said nucleic acid molecule may be increased in a subject, in a cell of said subject, in a tissue of said subject or in body fluid of said subject by increased concentration of said nucleic acid molecule in said cell, tissue or body fluid.

In the invention, a cell, a tissue, an organ or body fluid is preferably from a subject suspected to have a high risk of having a disease or condition associated with inflammation and/or coagulation and/or organ damage or failure due for example to its age or its genetic background or to its diet. Alternatively, in another preferred embodiment, the invention is applied on a cell, tissue, organ or body fluid from a subject diagnosed as either having a predictive risk for developing later a disease or condition associated with inflammation and/or coagulation and/or organ damage or failure. Alternatively, a cell, a tissue or organ to be treated may be selected based on risk of progression of the disease or condition associated with inflammation and/or coagulation and/or organ damage or failure. Such risk of progression may be assessed using classical clinic-pathological criteria or biomarker-based prognosis known to the skilled person. An example of a situation wherein coagulation may occur is DIC as explained in detail in the background of the invention. Causes underlying DIC may be an infectious organism, cancer, surgery or trauma, or others.

In the invention, a cell, a tissue, an organ or body fluid is preferably from a subject suspected to have a high risk of having a disease or condition associated with inflammation and/or coagulation and/or organ damage or failure and/or wherein an increase/upregulation of a parameter linked with inflammation or coagulation or organ damage or failure occur due for example to its age or its genetic background or to its diet or to the country wherein he lives or to DIC. Alternatively, in another preferred embodiment, the invention is applied on a cell, tissue, organ or body fluid from a subject diagnosed as either having a predictive risk for developing later a disease or condition associated with inflammation and/or coagulation and/or organ damage or failure and/or wherein an increase/upregulation of a parameter linked with inflammation or coagulation or organ damage or failure occur due for example to its age or its genetic background or to its diet or to the country wherein he lives or to DIC.

A nucleic acid molecule as identified herein has preferably an acceptable level of an anti-inflammatory and/or anti-coagulation and/or organ-protective activity. An acceptable level of an anti-inflammatory and/or anti-coagulation and/or organ-protective activity means at least 50%, 60%, 70%, 80%, 90%, 100% or more of the activity of the molecule represented by SEQ ID NO:1 or 2 measured in the same conditions. An acceptable level of anti-coagulation activity may also be equivalent with at least 50%, 60%, 70%, 80%, 90%, 100% or more of the activity of rivaroxaban measured in the same conditions.

The nucleic acid molecule or composition of the invention may be combined with standard treatments of disease or condition wherein inflammation and/or coagulation and/or organ damage or failure occur such as rivaroxaban or Warfarin as anti-coagulant.

In the context of the invention, preventing, treating, regressing, curing and/or delaying a disease or condition associated with inflammation and/or coagulation and/or organ damage or failure may mean that:

at least a symptom of this disease or condition has been improved, and/or at least a parameter associated with this disease or condition has been improved.

The improvement may be measured during at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days, one week, one month, six months of treatment or more. Preferred parameters associated with inflammation and/or coagulation and/or organ damage or failure have already been defined herein.

In the context of the invention, preventing, treating, regressing, curing and/or delaying a disease or condition associated with inflammation and/or coagulation and/or organ damage or failure may be replaced by achieving an anti-inflammation and/or an anti-coagulation and/or an organ-protective effect. Unless otherwise indicated, an anti-inflammatory and/or an anti-coagulation and/or an organ-protective effect is preferably assessed or detected before treatment and after at least one hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days, one week, two weeks, three weeks, four weeks, one month, two months, three months, four months, five months, six months or more in a treated subject.

An anti-inflammatory effect is preferably identified in a subject as:
- a detectable decrease of the expression level of a pro-inflammatory cytokine, preferably IL1beta, IL-6, TNFalpha and/or HMGB1 and/or
- a detectable increase of the expression level of an anti-inflammatory cytokine such as IL-10, and/or
- a decrease in the detection of the number of inflammatory infiltrates of leukocytes and/or
- a detectable decrease of the expression of a pro-inflammatory receptor such as MAC-1, P-selectin, EPCR and/or of CD36 and/or
- a detectable decrease of the expression of a pro-inflammatory receptor such as L-selectin, CD35, CD88, ICAM-1 and/or PECAM-1 and/or
- a detectable decrease of the serum level of fibrinogen, which is a positive acute-phase protein and/or
- a prolongation of patient survival of at least one month, several months or more (compared to those not treated or treated with a control or compared with the subject at the onset of the treatment).

In the context of the invention, a patient may survive and may be considered as being disease free. Alternatively, the disease or condition may have been stopped or delayed or regressed.

A detectable decrease of the expression level of IL1beta, IL-6, HMGB1 and/or TNFalpha may be a decrease of at least 5%, 10%, 20%, 30%, 40%, 50%, 55%, 60%, 65%, 70% or 75% or more. This decrease of expression level may be assessed using known techniques, preferably as assessed in the experimental part. The expression may be assessed at the RNA or protein level. Such decrease may be assessed after at least 3, 4, 5, 6, 7 days after transfection with a given nucleic acid molecule.

A detectable increase of the expression level of IL-10 may be an increase of at least 5%, 10%, 20%, 30%, 40%, 50%, 55%, 60%, 65%, 70% or 75% or more. This increase of expression level may be assessed using known techniques, preferably as assessed in the experimental part. The expression may be assessed at the RNA or protein level. Such increase may be assessed after at least 3, 4, 5, 6, 7 days after transfection with a given nucleic acid molecule.

A decrease in the detection of the number of inflammatory infiltrates of leukocytes may be a decrease of at least 1%, 5%, 10%, 15%, 20%, 25%, or more. Such increase may be assessed after at least 3, 4, 5, 6, 7 days after transfection with a given nucleic acid molecule. The detection of inflammatory infiltrates of leukocytes may be assessed using techniques known to the skilled person, preferably using immunofluorescence by FACS analysis.

A decrease of the expression of a pro-inflammatory receptor such as MAC-1, P-selectin, EPCR and/or CD36 may be a decrease of at least 1%, 5%, 10%, 15%, 20%, 25%, or more. The detection of such receptors may be assessed using techniques known to the skilled person, preferably using immunofluorescence by FACS analysis. Such increase may be assessed after at least 3, 4, 5, 6, 7 days after transfection with a given nucleic acid molecule.

A decrease of the expression of a pro-inflammatory receptor such as L-selectin, CD35, CD88, ICAM-1 and/or PECAM-1 may be a decrease of at least 1%, 5%, 10%, 15%, 20%, 25%, or more. The detection of such receptors may be assessed using techniques known to the skilled person, preferably using immunofluorescence by FACS analysis. Such increase may be assessed after at least 3, 4, 5, 6, 7 days after transfection with a given nucleic acid molecule.

A decrease of the serum level of fibrinogen, which is a positive acute-phase protein, may be a decrease of at least 5%, 10%, 20%, 30%, 40%, 50%, 55%, 60%, 65%, 70% or 75% or more. The detection of fibrinogen may be assessed using techniques known to the skilled person, preferably as assessed in the experimental part. Such decrease may be assessed after at least 3, 4, 5, 6, 7 days after transfection with a given nucleic acid molecule.

An anti-coagulation effect is preferably identified in a subject as:
- a detectable increase of APTT and/or a detectable increase of anti-coagulant protein-S and/or a detectable increase of EPCR is observed and/or
- a detectable increase of thrombomodulin and/or a detectable increase in protein C and/or a detectable increase in PECAM-1 is observed and/or
- a detectable decrease of fibrin clot density and/or bleeding time is observed, and/or
- a decrease of thrombin formation and/or
- a decrease of D-dimers and/or
- a decrease of heparan sulfate and/or
- a prolongation of patient survival of at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days, one month, several months or more (compared to those not treated or treated with a control or compared with the subject at the onset of the treatment) and/or
- a detectable increase of fibrinolytic activity (increase of tPA, decrease of the complex between PAI-1 and tPA) and/or a detectable decrease of fibrinogen.

In the context of the invention, a patient may survive and may be considered as being disease free. Alternatively, the disease or condition may have been stopped or delayed or regressed.

A detectable increase of APTT and/or anti-coagulant protein-S and/or EPCR may be an increase of at least 5%, 10%, 20%, 30%, 40%, 50%, 55%, 60%, 65%, 70% or 75% or more. APTT, anti-coagulant protein-S and EPCR may be assessed using known techniques, preferably as assessed in the experimental part. Such increase may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable increase of thrombomodulin and/or protein C and/or PECAM-1 may be an increase of at least 5%, 10%, 20%, 30%, 40%, 50%, 55%, 60%, 65%, 70% or 75% or more. Thrombomodulin, protein C and PECAM-1 may be assessed using known techniques, preferably as assessed in the experimental part. Such increase may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable decrease of fibrin clot density and/or bleeding time may be a decrease of at least 5%, 10%, 20%, 30%, 40%, 50%, 55%, 60%, 65%, 70% or 75% or more. Fibrin clot density and bleeding time may be assessed using known techniques, preferably as assessed in the experimental part. Such decrease may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable decrease of thrombin formation may be a decrease of at least 5%, 10%, 20%, 30%, 40%, 50%, 55%, 60%, 65%, 70% or 75% or more. Thrombin formation may be assessed using known techniques, preferably as assessed in the experimental part. Such increase may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable decrease of D-dimers and/or heparan sulfate may be a decrease of at least 5%, 10%, 20%, 30%, 40%, 50%, 55%, 60%, 65%, 70% or 75% or more. D-dimers and/or heparan sulfate may be assessed using known techniques, preferably as assessed in the experimental part. Such increase may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable increase of fibrinolytic activity (increase of tPA) may be an increase of at least 5%, 10%, 20%, 30%, 40%, 50%, 55%, 60%, 65%, 70% or 75% or more. The detection of free active TPA may be assessed using known techniques, preferably as assessed in the experimental part. Such increase may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days transfection with a given nucleic acid molecule.

A detectable increase of fibrinolytic activity may also be assessed by a decrease of the complex between PAI-1 and tPA. Said decrease may be of at least 5%, 10%, 20%, 30%, 40%, 50%, 55%, 60%, 65%, 70% or 75% or more. The detection of PAI-1 and tPA may be assessed using known techniques, preferably as assessed in the experimental part. Such decrease may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days transfection with a given nucleic acid molecule.

A detectable increase of fibrinolytic activity may also be assessed by a decrease of fibrinogen. Said decrease may be of at least 5%, 10%, 20%, 30%, 40%, 50%, 55%, 60%, 65%, 70% or 75% or more. The detection of fibrinogen may be assessed using known techniques, preferably as assessed in the experimental part. Such decrease may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days transfection with a given nucleic acid molecule.

An organ-protective effect is preferably identified in a subject as:
- a detectable improvement in a parameter linked with organ damage or failure such as AST, ALT, GGT, ALP, LDH, creatine kinase, BUN, albumin, creatinine, glucose, bile acid, total bilirubin, conjugated bilirubin, phosphorus, total protein, LDL cholesterol, HDL cholesterol, cholesterol and/or triglycerides. Improvement is defined as an increase or decrease of a parameter value so that it comes closer to the normal range in a healthy subject.
- a prolongation of patient survival of at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days, one month, several months or more (compared to those not treated or treated with a control or compared with the subject at the onset of the treatment).

In the context of the invention, a patient may survive and may be considered as being disease free. Alternatively, the disease or condition may have been stopped or delayed or regressed.

A detectable improvement in AST and/or ALT and/or GGT and/or ALP and/or LDH and/or total bilirubin and/or conjugated bilirubin and/or BUN and/or creatine kinase and/or creatinine and/or bile acid and/or phosphorus and/or triglycerides and/or LDL cholesterol and/or HDL cholesterol and/or cholesterol may be a decrease of at least 5%, 10%, 20%, 30%, 40%, 50%, 60%, 70%, 80%, 90%, 100%, 150%, 200%, 300%, 400%, 500%, 600%, 700%, 800%, 900%, 10-fold, 20-fold, 30-fold, 40-fold, 50-fold, 60-fold, 70-fold, 80-fold, 90-fold or 100-fold or more. AST, ALT, GGT, ALP, LDH, total bilirubin, conjugated bilirubin, BUN, creatine kinase, creatinine, bile acid, phosphorus, triglycerides, LDL cholesterol, HDL cholesterol and cholesterol may be assessed using techniques known to the skilled person, preferably as done in the experimental part. Such decrease may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable improvement in albumin and/or total protein may be an increase of at least 5%, 10%, 20%, 30%, 40%, 50%, 55%, 60%, 65%, 70% or 75% or more. Albumin and total protein may be assessed using techniques known to the skilled person, preferably as done in the experimental part. Such increase may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

A detectable improvement in glucose may be an increase or decrease of at least 5%, 10%, 20%, 30%, 40%, 50%, 60%, 70%, 80%, 90%, 100%, 150%, 200%, 300%, 400%, 500%, 600%, 700%, 800%, 900% or 10-fold or more. Glucose may be assessed using techniques known to the skilled person. Such increase or decrease may be assessed after at least 1 hour, 2 hours, 3 hours, 4 hours, 5 hours, 6 hours, 7 hours, 8 hours, 9 hours, 10 hours, 11 hours, 12 hours, 16 hours, 18 hours, 20 hours, 22 hours, 24 hours, 28 hours, 32 hours, 36 hours, 40 hours, 44 hours, 48 hours, 52 hours, 56 hours, 60 hours, 64 hours, 68 hours, 72 hours, 78 hours, 82 hours, 86 hours, 90 hours, 94 hours, 4 days, 5 days, 6 days, 7 days, 10 days after transfection with a given nucleic acid molecule.

Therefore, in a preferred embodiment, a nucleic acid molecule as earlier defined herein is for use as a medicament as an anti-inflammatory and/or anti-coagulant and/or organ-protective medicament,
(a) wherein a parameter associated with inflammation such as the level of a pro-inflammatory cytokine, the level of a pro-inflammatory integrin and/or the number of pro-inflammatory infiltrates have been decreased and/or
(b) wherein a parameter associated with coagulation such as fibrin clot formation and/or thrombin concentration have been decreased and/or
(c) wherein a parameter associated with organ damage or failure such as AST, ALT, GGT, ALP, LDH, creatine kinase, BUN, albumin, creatinine, glucose, bile acid, total bilirubin, conjugated bilirubin, phosphorus, total protein, LDL cholesterol, HDL cholesterol, cholesterol and/or triglycerides has been improved.

In a further preferred embodiment, a nucleic acid molecule as earlier defined herein is for use as a medicament as an anti-inflammatory and/or anti-coagulant and/or organ-protective medicament,
(a) wherein a parameter associated with inflammation such as the level of a pro-inflammatory cytokine, the level of a pro-inflammatory integrin and/or the number of pro-inflammatory infiltrates have been decreased and/or
(b) wherein a parameter associated with coagulation such as fibrin clot formation and/or thrombin concentration have been decreased and/or
(c) wherein a parameter associated with organ damage or failure such as AST, ALT, GGT, ALP, LDH, creatine kinase, BUN, albumin, creatinine, glucose, bile acid, total bilirubin, conjugated bilirubin, phosphorus, total protein, LDL cholesterol, HDL cholesterol, cholesterol and/or triglycerides have been improved and/or
(d) wherein a parameter associated with immunostimulation has been increased.

Parameters associated with immunostimulation are known to the skilled person and include the activation of immune cells, preferably T, B and/or NK cells.

In a further aspect, there is provided a nucleic acid molecule for use preferably as earlier defined herein, wherein said use is as a medicament for preventing, treating, regressing, curing and/or delaying a disease or a condition wherein inflammation and/or coagulation and/or organ damage or failure occurs, wherein said nucleic acid molecule is represented by a nucleotide sequence that has at least 95% sequence identity with a nucleotide sequence comprising SEQ ID NO:1 or 2. Each feature of this further aspect has already been defined herein.

In a further aspect, there is provided the use of a nucleic acid or a composition comprising said nucleic acid molecule for the manufacture of a medicament for preventing, treating, regressing, curing and/or delaying a disease or a condition associated with inflammation and/or coagulation and/or organ damage or failure. Each feature of this further aspect has already been described herein.

In a further aspect, there is provided a method for preventing, treating, regressing, curing and/or delaying a condition or disease associated with inflammation and/or coagulation and/or organ damage or failure to a subject in the need thereof. Each feature of this further aspect has already been described herein.

In a preferred embodiment, a nucleic acid molecule for use, a composition for use, a use or a method as defined herein is for a disease or condition wherein inflammation and/or coagulation and/or organ damage or failure occur and which is preferably selected from rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, non-alcoholic steatosis, sarcoidosis, autoimmune diabetes, diabetes mellitus, uveitis, multiple sclerosis, Controlling Allograft Rejection after organ transplantation, graft versus host disease (GVHD), inflammatory lung diseases including asthma and chronic obstructive pulmonary disease (COPD), systemic lupus erythematosus (SLE), sarcoidosis, atopic dermatitis and cancer, acute coronary syndrome (ACS), thrombosis, peripheral vessel obstruction, obstructive arteriosclerosis, vasculitis, functional disorder occurring after heart surgery, complication caused by organ transplantation, angina pectoris, transient ischemic attack, toxemia of pregnancy (preeclampsia, eclampsia), diabetes, liver veno-occlusive disease (VOD), deep venous thrombosis (DVT), septic shock, severe sepsis, trauma, acute respiratory distress syndrome (ARDS) and disseminated intravascular coagulation (DIC), or a complication or an effect of the progression that is linked to one of these diseases or conditions.

In another preferred embodiment, a nucleic acid molecule for use, a composition for use, a use or a method as defined herein is for a disease or condition wherein inflammation and/or coagulation and/or organ damage or failure occur and which is preferably selected from infection, poisoning, aspiration syndromes, hypoperfusion or shock, heat-induced illness, ischemia, ischemia-reperfusion injury (IRI), autoimmune disease, hemorrhage, pancreatitis, bacteremia, burns, systemic inflammatory response syndrome (SIRS) and multiple organ failure or multiple organ dysfunction syndrome, or a complication or an effect of the progression that is linked to one of these diseases or conditions.

A preferred condition is DIC. Organ damage or failure is preferably liver damage or failure, kidney damage or failure.

General Definitions and General Technologies Referred to Herein

Nucleic Acids

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below.

Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids molecules of the invention will comprise, in some embodiments the of any described in SEQ ID NOs: 1 or 2. It is contemplated that nucleic acids sequences of the invention derived from SEQ ID NO: 1 or 2 can have, have at least, or have at most 85, 86, 87, 88, 89, 90, 91 contiguous nucleotides from SEQ ID NOs: 1 or 2 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the nucleic acid sequence of SEQ ID NOs: 1 or 2.

Nucleobases (or Bases)

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

The nucleic acid molecule may be further modified to obtain optimized/adequate binding affinities. The primary sequence may be modified. It is also possible to add hydrophobic moiety/moieties into the nucleic acid molecule to expand its diversity of interaction with targets. All these possibilities have been described in detail in Hasegawa H et. al which is incorporated by reference in this context.

The term "recombinant" may be used and this generally refers to a molecule that has been manipulated in vitro or that is the replicated or expressed product of such a molecule. Recombinant methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid. In addition to the use of recombinant technology, such non-synthetic nucleic acids may be generated chemically, such as by employing technology used for creating oligonucleotides.

Host Cells and Target Cells

The cells wherein a nucleic acid molecule of the invention is introduced or wherein the presence of said molecule is assessed may be derived from or contained in any organism. Preferably, the cell is a vertebrate cell. More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be qualified as epithelial cells, brain, breast, cervix, colon, gastrointestinal tract, heart, kidney, large intestine, liver, lung, ovary, pancreas, heart, prostate, bladder, small intestine, stomach, testes or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a nucleic acid molecule or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to brain, stem cells, liver, lung, bone, breast, cervix, colon, endometrium, epithelial, esophagus, goblet cells, kidney, ovaries, pancreas, prostate, bladder, skin, small intestine, stomach, testes, heart.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid to a cell. This may be done as part of a therapeutic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described.

Modes of Administration and Formulations

A nucleic acid molecule of the invention may be present in a composition, preferably a pharmaceutical composition. The nucleic acid molecule of the invention may be administered to a subject alone or in the form of a composition or pharmaceutical composition for the treatment of a condition or disease as defined herein. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen. For topical administration the proteins of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The nucleic acid molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed.

Liposomes and emulsions are well-known examples of delivery vehicles that may be used to deliver nucleic acids of the invention.

A nucleic acid of the invention may be administered in combination with a carrier or lipid to increase cellular uptake. For example, the nucleic acid molecule may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine.

Nucleic acids may also be conjugated to a chemical moiety, such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates; small molecules including naproxen, ibuprofen or other known protein-binding molecules, cyclodextrin, which targets the transferrin receptor (Hu-Lieskovan et al., 2005), PEI (RGD-targeted PEG-PEI, Schiffelers et al. 2004), anisamide, RGD-peptide or RGD mimics, poly-arginin, anti-TfR single chain antibody fragment/TfRscFv, Annexin A5 (targeting phophatidylserine exposing membranes, Garnier et al., 2009, 11:2114-22), WO 2009/126933 describing compositions and methods for site-specific delivery of nucleic acids by combining them with targeting ligands and endosomolytic components. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of the nucleic acid molecules dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of an pharmaceutical composition that contains at least one nucleic acid molecule will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The nucleic acid molecules may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise less than 1 microgram/kg body weight, or 1 microgram/kg body weight, from 5 microgram/kg body weight, 10 microgram/kg body weight, 50 microgram/kg body weight, 100 microgram/kg body weight, 200 microgram/kg body weight, 350 microgram/kg body weight, 500 microgram/kg body weight, 1 milligram/kg body weight, 5 milligram/kg body weight, 10 milligram/kg body weight, 50 milligram/kg body weight, 100 milligram/kg body weight, 200 milligram/kg body weight, 350 milligram/kg body weight, or 500 milligram/kg body weight, to 1000 mg/kg body weight or more per administration, and any range derivable therein. In non-limiting examples of a derivable range from the numbers listed herein, a range of 5 mg/kg body weight to 100 mg/kg body weight, 5 microgram/kg body weight to 500 milligram/kg body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compound may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both. The composition must be stable under the conditions of manufacture and storage, and preserved against the contaminating action of microorganisms, such as bacteria and fungi.

It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms or parameters associated with inflammation or coagulation as earlier defined herein, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: The Pharmacological Basis of Therapeutics, Ch. 1, p. 1).

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-ammoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe (II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a nucleic acid molecule or composition comprising said nucleic acid molecule as defined herein may comprise additional component(s) than the ones specifically identified, said additional component(s) not altering the unique characteristic of the invention. In addition the verb "to consist" may be replaced by "to consist essentially of" meaning that a method as defined herein may comprise additional step(s) than the ones specifically identified, said additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Figure 1:
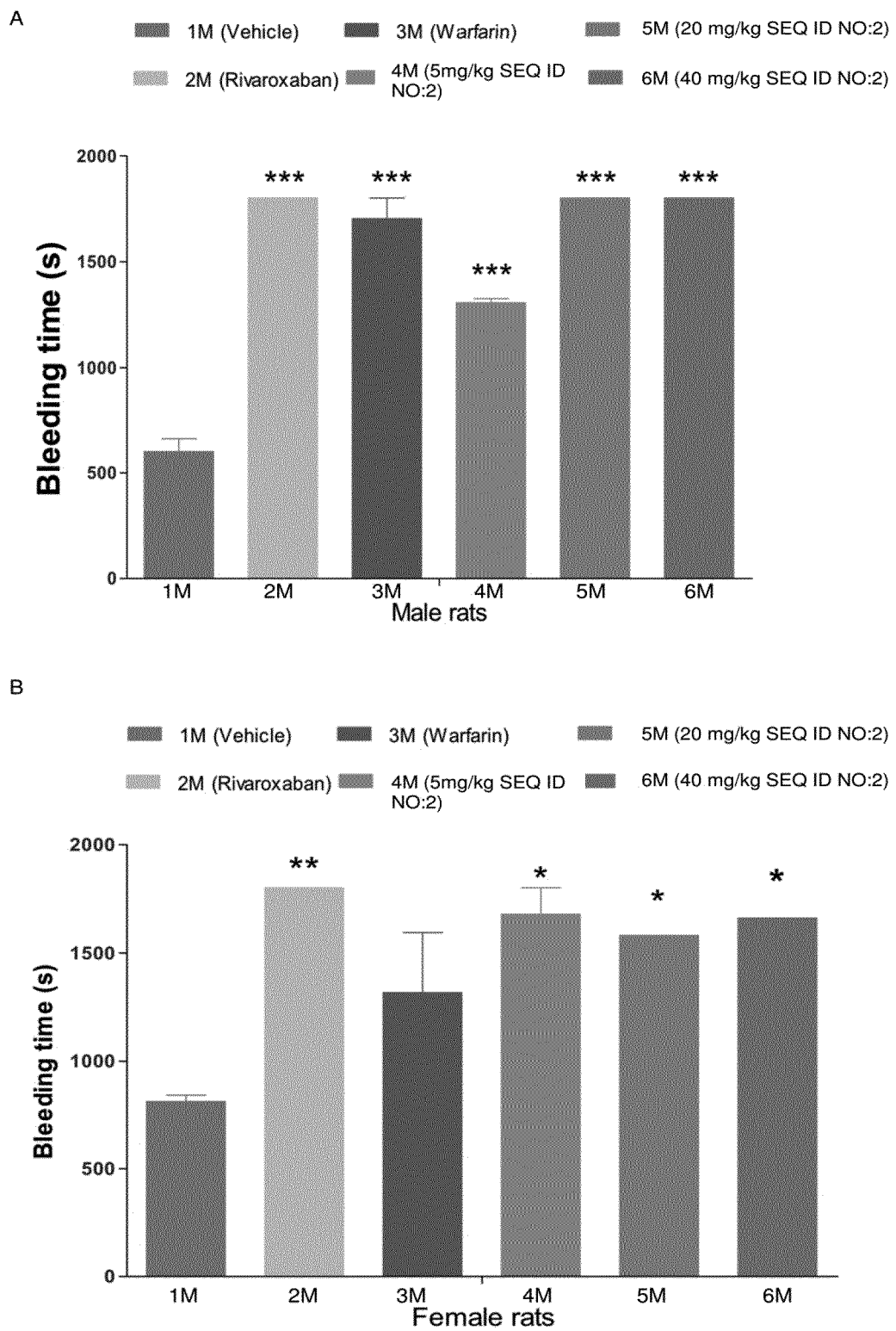
FIG. 1: Anti-coagulant activity of SEQ ID NO:2 in tail Bleeding Model. Rats were intravenously injected with SEQ ID NO:2 at dose levels of 5, 20 and 40 mg/kg saline solution. As a positive control, Rivaroxaban and Warfarin. Rivaroxaban was administered by oral gavage 1 hour before bleeding time assay. Bleeding time was measured both in male (A) and female (B) rats, 5 minutes after injection or 1 hour after oral gavage. Each bar represents the means±SE (one-way ANOVA followed by Dunnett's Multiple Comparison post Test; *$p \le 0.05$, $p < 0.01$ and *$p < 0.001$).

Study 1: Anti-Coagulant Effect of SEQ ID NO:2

Example 1: Anti-Coagulant Activity of SEQ ID NO:2. Tail Bleeding Model

Materials and Methods

Rats

A total of 36 Sprague-Dawley male and female rats were utilized and divided into six groups comprising of 6 animals per group. Animal handling was performed according to guidelines of the National Institute of Health and the Association for Assessment and Accreditation of Laboratory Animal Care. Animals were fed ad libitum a commercial rodent diet (Teklad Certified Global 18% Protein Diet cat #: 2018SC). Animals had free access to autoclaved and acidified drinking water (pH between 2.5 and 3.5) obtained from the municipality supply. Animals were housed under standard laboratory conditions, air conditioned and filtered with adequate fresh air supply. Animals were kept in a climate controlled environment.

Compounds and Formulation

SEQ ID NO:2 (Biospring) (100 mg) was dissolved in 5 ml saline to form a stock solution of 20 mg/ml. Vehicle (saline) was provided by Pharmaseed as ready to use for i.v. administration. Rivaroxaban (Bayer, Pharmaseed Ltd) dosing solution was diluted at 10 mg/kg (Group 2M). Warfarin (Ceriliant, Pharmaseed Ltd) was diluted at 0.5 mg/kg (Group 3M). Both Rivaroxaban and Warfarin are clinical standards with anticoagulation activity. To obtain SEQ ID NO:2 dosing solution (2.5 mg/ml) for dose level of 5 mg/kg and dose volume of 2 ml/kg for i.v. injection, 0.375 ml of the above 20 mg/ml stock solution was diluted with 2.625 ml of saline (Group 4M). To obtain SEQ ID NO:2 dosing solution (10 mg/ml) for dose level of 20 mg/kg and dose volume of 2 ml/kg for i.v. injection, 1.5 ml of the above 20 mg/ml stock solution was diluted with 1.5 ml saline (Group 5M). To obtain SEQ ID NO:2 dosing solution (20 mg/ml) for dose level of 40 mg/kg and dose volume of 2 ml/kg for i.v. injection, the above 20 mg/ml stock used (Group 6).

Compound Administration

Rats were intravenously injected five minutes before bleeding time assay. The amount of rats per group are displayed in Table 1. Three treated groups received SEQ ID NO:2 at dose levels of 5, 20 and 40 mg/kg saline solution. In each gender, control groups received saline Vehicle. A positive control group received Rivaroxaban (10 mg/kg). Rivaroxaban was administered by oral gavage 1 hour before bleeding time assay. A second positive control groups received Warfarin (0.5 mg/kg).

TABLE 1

| treatment regimen | | | | |
|---|---|---|---|---|
| Group | Animals ID | Treatment | Dose level (mg/kg) | ROA |
| 1 M, 1 F | Male (1, 2, 3) Female (19, 20, 21) | Vehicle | NA | IV |
| 2 M, 2 F | Male (4, 5, 6) Female (22, 23, 24) | Rivaroxaban | 10 | PO |
| 3 M, 3 F | Male (7, 8, 9) Female (25, 26, 27) | Warfarin | 0.5 | IV |
| 4 M, 4 F | Male (10, 11, 12) Female (28, 29, 30) | SEQ ID NO: 2 | 5 | IV |

TABLE 1-continued treatment regimen

| Group | Animals ID | Treatment | Dose level (mg/kg) | ROA |
|---|---|---|---|---|
| 5 M, 5 F | Male (13, 14, 15) Female (31, 32, 33) | SEQ ID NO: 2 | 20 | IV |
| 6 M, 6 F | Male (16, 17, 18) Female (34, 35, 36) | SEQ ID NO: 2 | 40 | IV |

Tail Bleeding Time Measurements

Male and female rats were anaesthetized by intraperitoneal injection of ketamine/xylazine. Bleeding time was monitored as described in Stupnisek et al. (2012), until blood flow stopped for a complete 30-sec interval or till the end of 30 min period. In deeply anaesthetized rats (placed in ventral position) the tail was transected with a surgical scalpel 2 mm from the tip (and submerged into a tube with 40 ml of saline at room temperature in vertical position) and the duration and amount of bleeding was measured to evaluate the hemostatic effect of the agents or saline administration. Following the completion of bleeding time evaluation, all rats were immediately sacrificed by CO2 asphyxiation.

Statistical Analysis

Numerical results were given as means±standard errors. If applicable, statistical analysis was carried out using one-way ANOVA followed by Dunnett's Multiple Comparison post Test. A probability of 5% (p≤0.05) was regarded as significant. In the figures, the degree of statistically significant differences between groups were illustrated as *p<0.05, p<0.01 and *p<0.001.

Results and Discussion

The antithrombotic activity of SEQ ID NO:2 given intravenously in three different doses was evaluated in rats. As shown in FIG. 1, group average bleeding time was increased significantly in all treated groups both in males (FIG. 1A) and females (FIG. 1B) compared to the matched vehicle group (1M). A comparable bleeding time was measured between the positive control groups (Rivaroxaban and Warfarin) and all doses of SEQ ID NO:2 tested both in male (FIG. 1A) and female rats (FIG. 1B). Bleeding time in the matched treated groups was similar in both male and female rats. A dose response effect of SEQ ID NO:2 can be observed in male but not in female rats.

SEQ ID NO:2 demonstrated a clear anticoagulation effect on the bleeding time in both animal genders (male and female). However, only in male rats, a dose response anticoagulation effect of SEQ ID NO:2 was observed. The anti-coagulation activity of SEQ ID NO:2 at all doses was equivalent to the activity of clinical care standards (Rivaroxaban and Warfarin).

Example 2: Anti-Coagulant Activity of SEQ ID No:2. Arteriovenous Shunt Model

Materials and Methods

Rats

This study was conducted at Shanghai WuXi AppTec Co., Ltd., and in accordance with WuXi IACUC standard animal procedures along with the IACUC guidelines that are in compliance with the Animal Welfare Act, the Guide for the Care and Use of Laboratory Animals, and the Office of Laboratory Animal Welfare (OLAW). Sprague-Dawley male rats with body weight ranging between 150-200 g (Vital River; Bejing, P.R. China) were fed ad libitum a rodent diet. Animals had free access to autoclaved and acidified drinking water. Animals were housed under standard laboratory conditions, air conditioned and filtered with adequate fresh air supply. Animals were kept in a climate controlled environment.

Compounds

Rivaroxaban (10 mg/kg) has been dissolved in water and stored at 4° C. 20 mg SEQ ID NO:2 (Biospring) was dissolved in 3 ml Saline, vortexed for 5 min., sonicated with a water bath ultrasonic for 1 minute to achieve 6.66 mg/ml SEQ ID NO:2.

SEQ ID NO:2 Administration

The animals were assigned to 3 dosing groups according to the body weight (see table 2). Vehicle treated animals were intravenously injected with saline 90 min prior to shunt assay. The positive control treated animals were orally given Rivaroxaban 10 mg/kg at 90 min prior to shunt assay. SEQ ID NO:2 was intravenously injected 5 min prior to shunt assay. The dose volumes are displayed in table 2.

TABLE 2 treatment regimen

| Group | Animal Number (M) | Treatment | Route | Dose Volume |
|---|---|---|---|---|
| Vehicle 90 min | 8 | Saline | i.v. | 5 ml/kg |
| Rivaroxaban- 10 mg/kg 90 min | 8 | Rivaroxaban | p.o. | 5 ml/kg |
| Apta-1-33.3 mg/kg 5 min | 3 | Apta-1 | i.v. | 5 ml/kg |

Thrombus Measurements (Arteriovenous Shunt Test)

Rats were anesthetized with pentobarbital sodium (i.p., 50 mg/kg, 20 mg/mL, 2.5 ml/kg) 60 min prior to the shunt assay. The left jugular vein and the right common carotid artery were separated and cannulated with two 6 cm-long, saline-filled PE-60 catheters. The polyethylene catheters (American Health and Medical Supply International Corp.) were connected with an 8 cm-long PE-160 polyethylene tube containing a 6 cm-long rough nylon thread (size: 3-0, weight 3.5 mg) folded into a double string. Extracorporeal circulation was maintained for 15 min, the thrombus weight formed on the thread was calculated by subtracting the average weight of the rough nylon thread.

Activated Partial Thromboplastin Time (APTT) Measurements

Blood samples (2 ml) were withdrawn from the carotid artery catheter and collected into plastic tubes containing 1/10 volume of 3.2% trisodium citrate immediately after thrombus removal. Subsequently, the samples were centrifuged at 7000 rpm for 10 min at 4° C. for plasma collection. Samples for APTT analysis were analyzed in duplicate by Labmedicin Skåne utilizing a BCS-XP Coagulation Analyzer (Siemens Marburg, Germany) according to the manufacturer's protocol. Reagents used are APTT reagent Actin FSL (Siemens, Marburg, Germany) and sterile 0.9% NaCl.

Statistical Analysis

Significance of difference between control and treated groups was analyzed by performing analysis of variance (ANOVA) by EXCEL office software. P value less than 0.05 was considered statistically significant.

Results and Discussion

Figure 2:
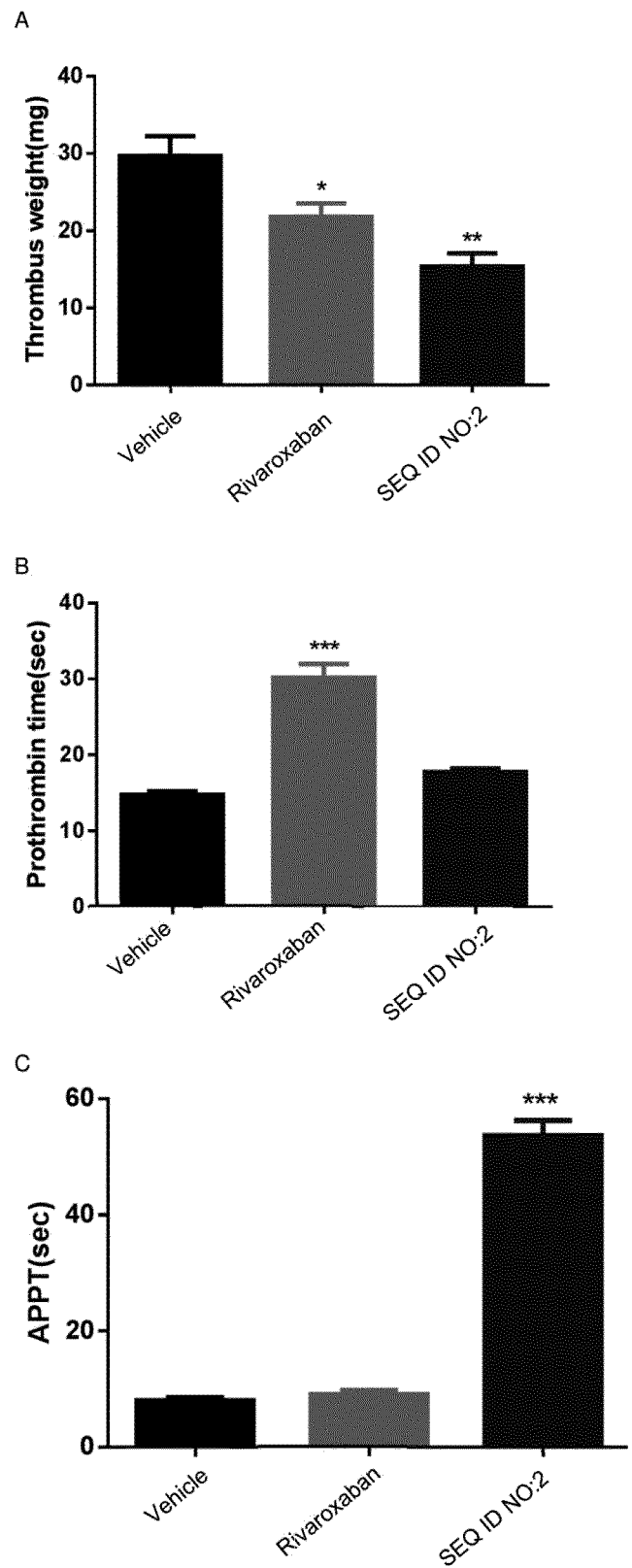
FIG. 2: Anti-coagulant activity of SEQ ID NO:2 in Arteriovenous Shunt model. Male rats were intravenously injected with saline (Vehicle) or SEQ ID NO:2 solution, according to their body weight. Rivaroxaban was orally administered to the positive control group. 5 to 90 minutes after administration, rats were anesthetized with pentobarbital-na (50 mg/kg). The left jugular vein and the right carotid artery of anesthetized rats were connected with two catheters. The thrombus weight formed on the thread was calculated by subtracting the average weight of the rough nylon thread (A). Prothrombin times were measured (B) and Activated partial thromboplastin times (APTT) were analysed (C). Each bar represents the mean±SEM (n=8 for vehicle and rivaroxaban groups, n=3 for SEQ ID NO:2 group), *$p < 0.05$, $p < 0.01$, *$p < 0.001$ vs Vehicle.

As shown in FIG. 2A, SEQ ID NO2 treated rats showed significantly lower thrombus weight comparing to the vehicle group (48.1% less than vehicle group). The positive control group, which were dosed with Rivaroxaban 90 min before extracorporeal circulation, also formed significantly reduced thrombus (26.5% less than vehicle group).

As shown in FIG. 2B, positive control rivaroxaban significantly prolonged Prothrombin times, while SEQ ID NO:2 group did not show any significant difference compared to the vehicle group. As shown in FIG. 2C, rats treated with SEQ ID NO:2 showed significant increase in Activated Partial Thromboplastin Time (APTT), while positive control rivaroxaban did not show any different comparing to vehicle group. These positive effect of SEQ ID NO:2 on APTT has been confirmed in mouse, canine, non-human primate and human by comparable ex vivo studies.

In the rat arteriovenous Shunt model, SEQ ID NO:2 significantly reduced thrombus weight, demonstrating its anti-thrombotic effect. Positive compound Rivaroxaban also significantly inhibits thrombus formation, although the effect was not as potent as compound SEQ ID NO:2.

Whereas SEQ ID NO:2 had no effect on prothrombin time, it does prolong activated partial thromboplastin time (APTT). This might indicate that inhibition of thrombus formation by SEQ ID NO:2 would be mainly from the prolongation of activated partial thromboplastin time while rivaroxaban was mainly due to prolongation of prothrombin time.

Example 3: Anti-Coagulant Activity of SEQ ID NO:2 in Ferric Chloride Induced Arterial Thrombosis Model Materials and Methods
Rats Animal handling was performed according to guidelines of the National Institute of Health (NIH) and the Association for Assessment and Accreditation of Laboratory Animal Care (AAALAC). A total of 36 Sprague-Dawley rats (Envigo RMS) were divided into six groups comprising of 6 animals per group (3 males and 3 females). Sprague-Dawley male rats had an average body weight of 350 g at the beginning of the study. Female rats had a body weight of 243 g. Both were fed ad libitum a rodent diet. Animals had free access to autoclaved and acidified drinking water. Animals were housed under standard laboratory conditions, air conditioned and filtered with adequate fresh air supply. Animals were kept in a climate controlled environment.

Compounds and Formulation

SEQ ID NO:2 (Biospring) (100 mg) was dissolved in 5 ml saline to form a stock solution of 20 mg/ml. Vehicle (saline, Teva) as ready to use for i.v. administration. Rivaroxaban (Bayer, Pharmseed Ltd) dosing solution was diluted at 10 mg/kg (Group 2M). Warfarin (Ceriliant, Pharmaseed Ltd) was diluted at 0.5 mg/kg (Group 3M). Both Rivaroxaban and Warfarin are clinical standards with anticoagulation activity. To obtain SEQ ID NO:2 dosing solution (2.5 mg/ml) for dose level of 5 mg/kg and dose volume of 2 ml/kg for i.v. injection, 0.375 ml of the above 20 mg/ml stock solution was diluted with 2.625 ml of saline (Group 4M). To obtain SEQ ID NO:2 dosing solution (10 mg/ml) for dose level of 20 mg/kg and dose volume of 2 ml/kg for i.v. injection, 1.5 ml of the above 20 mg/ml stock solution was diluted with 1.5 ml saline (Group 5M). To obtain SEQ ID NO:2 dosing solution (20 mg/ml) for dose level of 40 mg/kg and dose volume of 2 ml/kg for i.v. injection, the above 20 mg/ml stock used (Group 6).

Compound Administration

Six groups, each comprising of six rats per group (3 males and 3 females), were assigned to the study. In each gender, a control group of 1 male and 1 female rat was intravenously (i.v.) injected with Vehicle. A first positive control group of 2 male and 2 female were orally treated with Rivaroxaban (10 mg/kg), 1 hour prior to the ferric chloride assay. A second positive control group, consisting 3 male and 3 female rats, were intravenously injected with Warfarin (0.5 mg/kg) 5 minutes prior to the ferric chloride assay. At last, three groups (consisting of 4-6 M and 4-6 F) were intravenously injected with SEQ ID NO:2 at dose levels of 5, 20 and 40 mg/kg, 5 minutes before ferric chloride assay.

Ferric Chloride Induced Arterial Thrombosis

Male and Female rats were anaesthetized by intraperitoneal injection of ketamine/xylazine. Arterial thrombus formation was performed as described by Lee J. et al., (2009). The right carotid artery was isolated and dissected free of the vagus nerve and surrounding tissues. Arterial thrombus formation was induced by wrapping a 2-mm$^2$ Whatman Grade 1 filter paper, saturated with 50% ferric chloride ($FeCl_3$; w/v, in distilled water), on the right carotid artery for 10 min. The time needed for occlusion to occur was measured for up to 60 min, and occlusion time was assigned a value of 60 min for vessels that were occlude within that time.

Cloth Formation Measurement

Clot formation was followed for 60 minutes following application of $FeCl_3$. After completion of clotting time evaluation, all rats were immediately sacrificed by Pental overdose. The artery wall was cut longitudinally; clot was taken out, weighed and measured by caliper.

Statistical Analysis

Numerical results were given as means±SE. If applicable, statistical analysis was carried out using two-way or one-way ANOVA followed by Bonferroni post-hoc test. A probability of 5% ($p \leq 0.05$) was regarded as significant. In the figures, the degree of statistically significant differences between groups were illustrated as *$p<0.05$, $p<0.01$ and *$p<0.001$.

Results and Discussion

Figure 3:
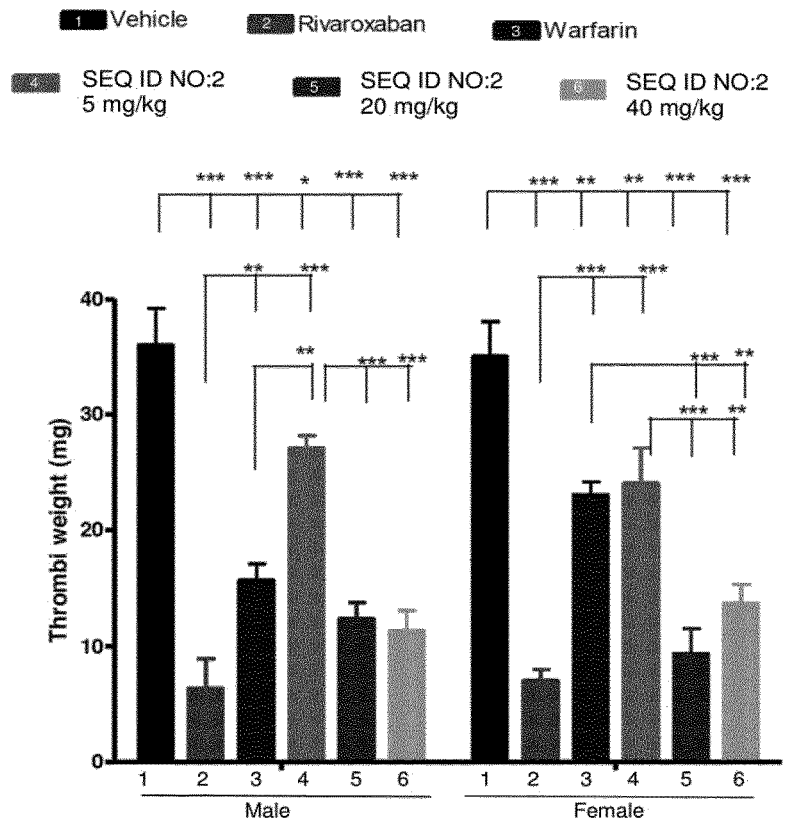
FIG. 3: Anti-coagulant activity of SEQ ID NO:2. in ferric chloride induced arterial thrombosis model. Prior to ferric chloride induced arterial thrombosis, mice were treated with 3 doses of SEQ ID NO:2. Mice were intravenously injected with NO:2 at dose levels of 5, 20 and 40 mg/kg, 5 minutes before the ferric chloride assay. Arterial thrombus formation was performed to measure both thrombi formation weight (A) and size (B). Each bar represents the mean+−SE (two-way ANOVA statistical analysis followed by Bonferroni post-hoc comparisons; *p<0.05; p<0.01;*p<0.001).
Figure 3:
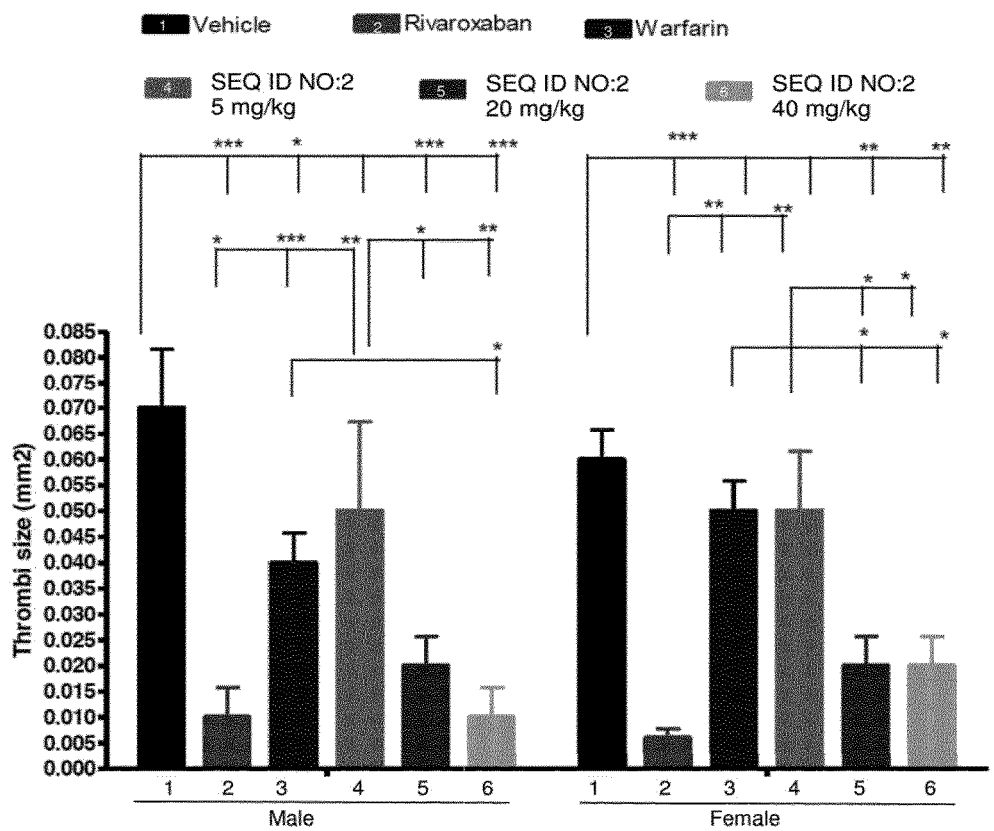

Clot formation was followed for 60 minutes following application of $FeCl_3$. Clot weight (FIG. 3A) and size (FIG. 3B) reduction was observed in all treated groups (positive controls and SEQ ID NO:2) compared to the control group (Vehicle). Male rats SEQ ID NO:2 treated with the lowest dose (5 mg/kg) showed statistically significant differences in the clot size (FIG. 3B) and weight (FIG. 3A) compared to Rivaroxaban positive control and SEQ ID NO:2 in high doses.

Study 2. Anti-Inflammatory Activities of SEQ ID NO:2

Example 4: Effects of Treatment on Cytokine Release after LPS Injection in C57BL/6 Mice Materials and Method
Mice Female C57BL/6 mice (Taconic Biosciences) were 8 weeks of age at the start of the study. Animals had free access to autoclaved and acidified drinking water. Animals were housed under standard laboratory conditions, air conditioned and filtered with adequate fresh air supply. Animals were kept in a climate controlled environment.

Compounds

SEQ ID NO:2 (Biospring) (100 mg) was dissolved in 5 ml saline to form a stock solution of 20 mg/ml. Vehicle is saline solution.

Dexamethasone stock was prepared by mixing dexamethasone and beta-cyclodextrin at a 4:96 ratio, solubilized in PBS at 2 mg dexamethasone/mL and stored at −20° C. Dosing solution of dexamethasone was prepared by diluting the stock solution to 1 mg/mL with PBS. Dexamethasone administered at 5 to 10 mg/kg, i.p. is used as a positive control for suppression of the immune response.

Compound Administration

Mice were dosed as displayed in table 3, five minutes prior to intravenous lipopolysaccharide (LPS) injection (100 ng/200 µl).

TABLE 3 treatment regimen

| Group | # mice | Treatment | Dose | Route | Frequency | Volume | Purpose |
|---|---|---|---|---|---|---|---|
| 1 | 10 | Vehicle | — | i.v. | once | 10 mL/kg | Negative control |
| 2 | 10 | Dexamethasone | 10 mg/kg | i.p. | once | 10 mL/kg | Positive control |
| 3 | 10 | SEQ ID NO: 2 | 5 mg/kg | i.v. | once | 10 mL/kg | Test |
| 4 | 10 | SEQ ID NO: 2 | 25 mg/kg | i.v. | once | 10 mL/kg | Test |
| 5 | 10 | SEQ ID NO: 2 | 50 mg/kg | i.v. | once | 10 mL/kg | Test |

Cytokine Measurements

Two hours after LPS injection mice were bled and serum was isolated and added to EDTA in Gel Clot Activator tubes. At least 100 µl has been analysed. The concentration of IL-10, TNF, IL-6 and IL-1β in serum was measured using eBioscience's Luminex kit, according to manufacturer's protocol. A single analysis was performed on every sample.

Results

To determine the anti-inflammatory activity of SEQ ID NO:2, mice were treated with SEQ ID NO:2 prior to LPS stimulation. Multiple pro-inflammatory cytokines (TNF, IL-6 and IL-1β) and the anti-inflammatory cytokine IL-10, have been assessed in serum sample from treated mice.

Figure 4:
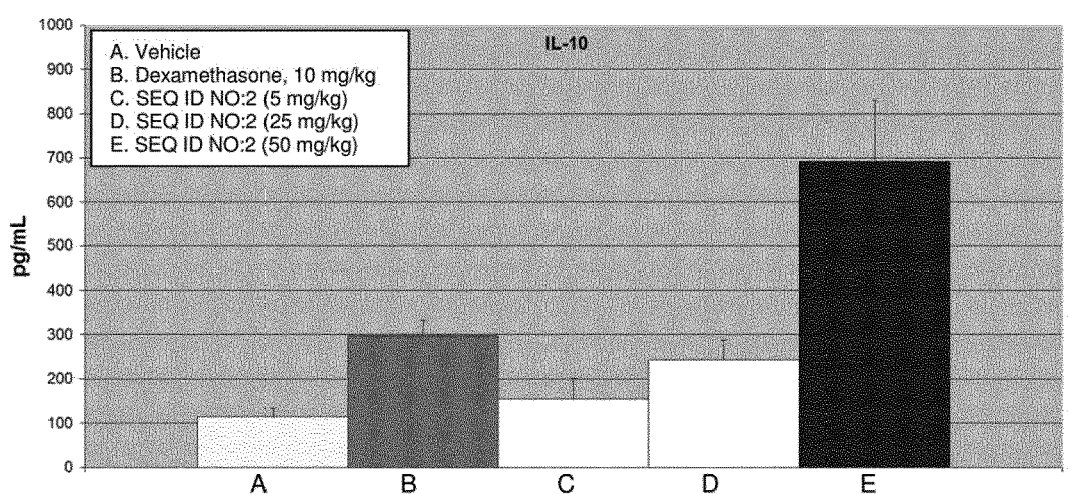
FIG. 4: Anti-inflammatory cytokine production induced by LPS injection in C57BL/6 mice. Mice were dosed with vehicle (negative control), dexamethasone (positive control), or customer compound (1 of 3 doses), then 5 minutes later injected with LPS. Two (2) hours after LPS injection mice were bled and serum was isolated. The concentration of IL-10, TNF, IL-6 and IL-1β in serum was measured using eBioscience's Luminex kit. Each bar represents the mean±SEM (n=8 for vehicle and rivaroxaban groups, n=3 for SEQ ID NO:2 group), *p<0.05, p<0.01, *p<0.001 vs Vehicle.
Figure 4:
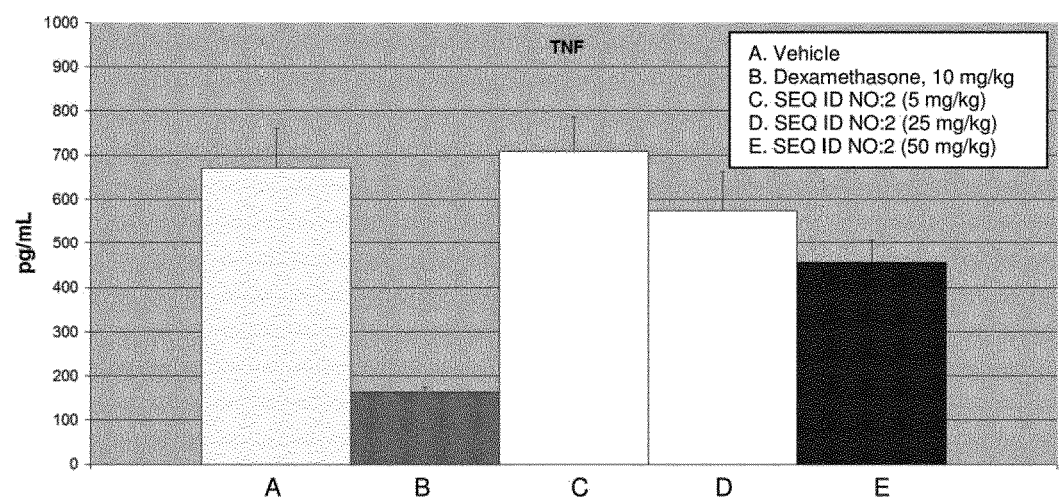
Figure 4:
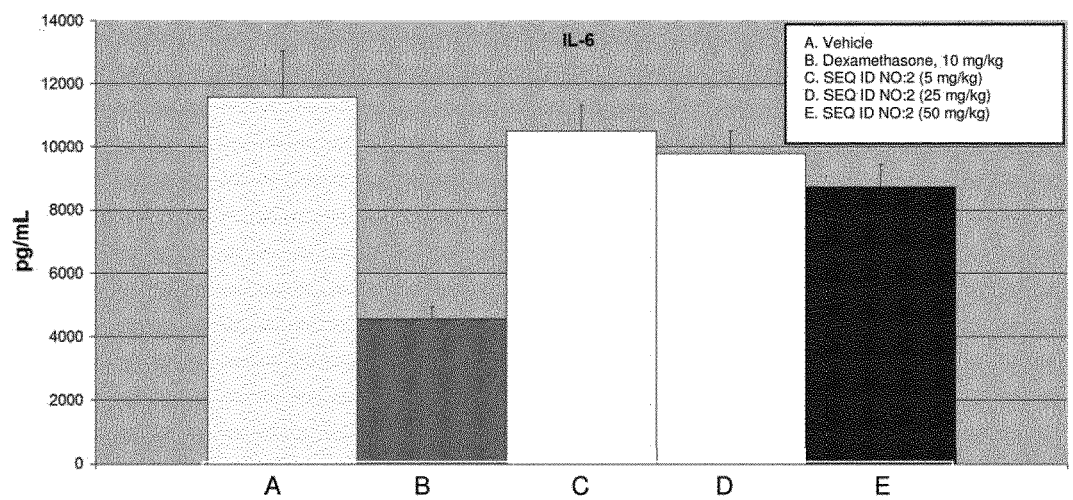
Figure 4:
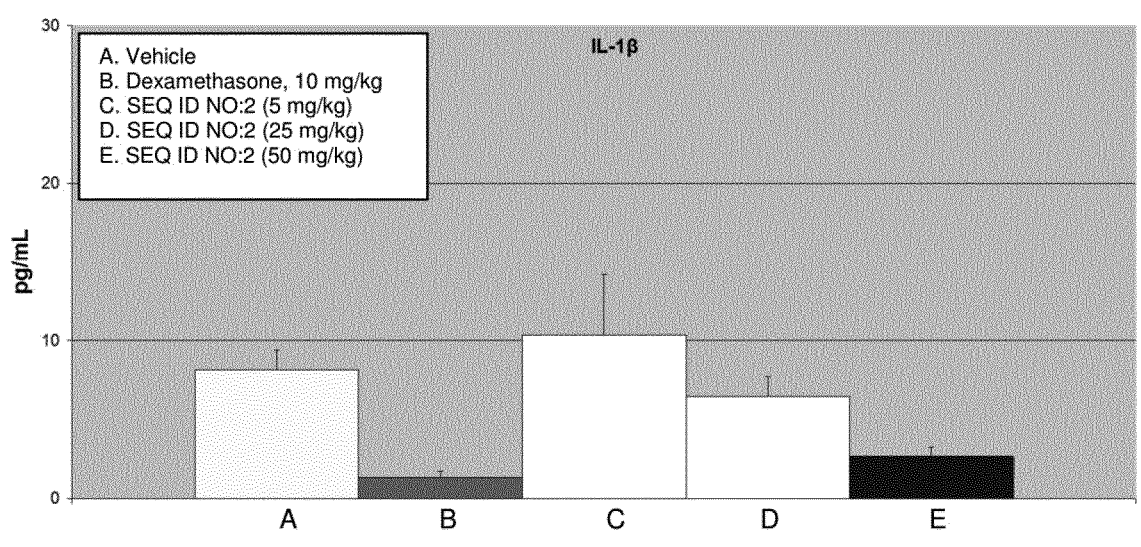

Serum concentration of IL-10 is shown in FIG. 4A. An increase in IL-10 compared to the vehicle group is seen for SEQ ID NO:2, and the differences were significant in the groups dosed at 25 and 50 mg/kg.

It can be seen from FIGS. 4B, 4C and 4D that the group dosed with SEQ ID NO:2 at 5 mg/kg had similar cytokine concentrations in serum to the vehicle group.

Groups dosed with SEQ ID NO:2 at 25 and 50 mg/kg had lower concentrations of TNF, IL-6 and IL-1β in serum, but only the reduction in IL-1β concentration in the group dosed at 50 mg/kg was statistically significant compared to the vehicle group.

Taken together, these results indicate that SEQ ID NO:2 has anti-inflammatory properties in the LPS-induced cytokine production model.

Example 5: Effect of SEQ ID NO:2 Treatment on Cell-Based Immune Responses after LPS Injection in C57BL/6 Mice Materials and Methods Mice Female C57BL/6 mice (Taconic Biosciences) were 8 weeks of age at the start of the study. Animals had free access to autoclaved and acidified drinking water. Animals were housed under standard laboratory conditions, air conditioned and filtered with adequate fresh air supply. Animals were kept in a climate controlled environment.

Compounds

SEQ ID NO:2 (Biospring) (100 mg) was dissolved in 5 ml saline to form a stock solution of 20 mg/ml. Vehicle is saline solution.

Dexamethasone stock was prepared by mixing dexamethasone and beta-cyclodextrin at a 4:96 ratio, solubilized in PBS at 2 mg dexamethasone/mL and stored at −20° C. Dosing solution of dexamethasone was prepared by diluting the stock solution to 1 mg/mL with PBS. Dexamethasone administered at 5 to 10 mg/kg, i.p. is used as a positive control for suppression of the immune response.

Compound Administration

Mice were dosed as displayed in table 4, five minutes prior to intravenous lipopolysaccharide (LPS) injection (100 ng/200 µl).

TABLE 4

| Group | # mice | Treatment | Dose | Route | Frequency | Volume | Purpose |
|---|---|---|---|---|---|---|---|
| 1 | 10 | Vehicle | — | i.v. | once | 10 mL/kg | Negative control |
| 2 | 10 | Dexamethasone | 10 mg/kg | i.p. | once | 10 mL/kg | Positive control |
| 3 | 10 | SEQ ID NO: 2 | 5 mg/kg | i.v. | once | 10 mL/kg | Test |
| 4 | 10 | SEQ ID NO: 2 | 25 mg/kg | i.v. | once | 10 mL/kg | Test |
| 5 | 10 | SEQ ID NO: 2 | 50 mg/kg | i.v. | once | 10 mL/kg | Test |

Flow Cytometry

Two hours after LPS injection mice were bled and blood samples were taken. Flow cytometry study was performed on BD FACSCalibur (lasers: 488 nm; 635 nm and UV). In our study we measured the expression of integrin Mac-1 (CD11b/18) on leukocytes by means of flow cytometry. Expression of CD11b on all leukocytes monocytes and granulocytes were assessed by flow cytometry using double fluorescence staining (CD 45/CD11b).

Results and Discussion

Figure 5:
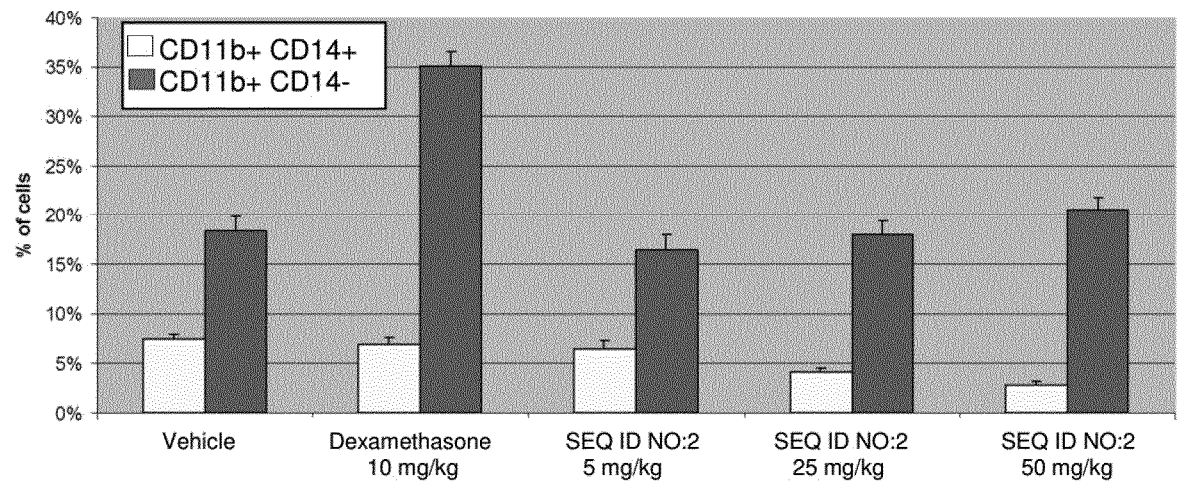
FIG. 5: Effect of SEQ ID NO:2 on cellular immune responses elicited by LPS injection in C57BL/6 mice. C57BL/6 mice were injected with SEQ ID NO:2 at 5, 25 and 50 mg/kg 5 minutes prior to intravenous LPS injection. Two hours after LPS injection, blood samples were taken. Blood samples were prepared for Flow cytometry analysis to determine the expression of CD11b and CD14. The amounts of CD11b+CD14+ and CD11b+CD14-white blood cells have been assessed. Each bar represents the mean±SEM (n=8 for vehicle and rivaroxaban groups, n=3 for SEQ ID NO:2 group), *p<0.05, p<0.01, *p<0.001 vs Vehicle.
Figure 5:
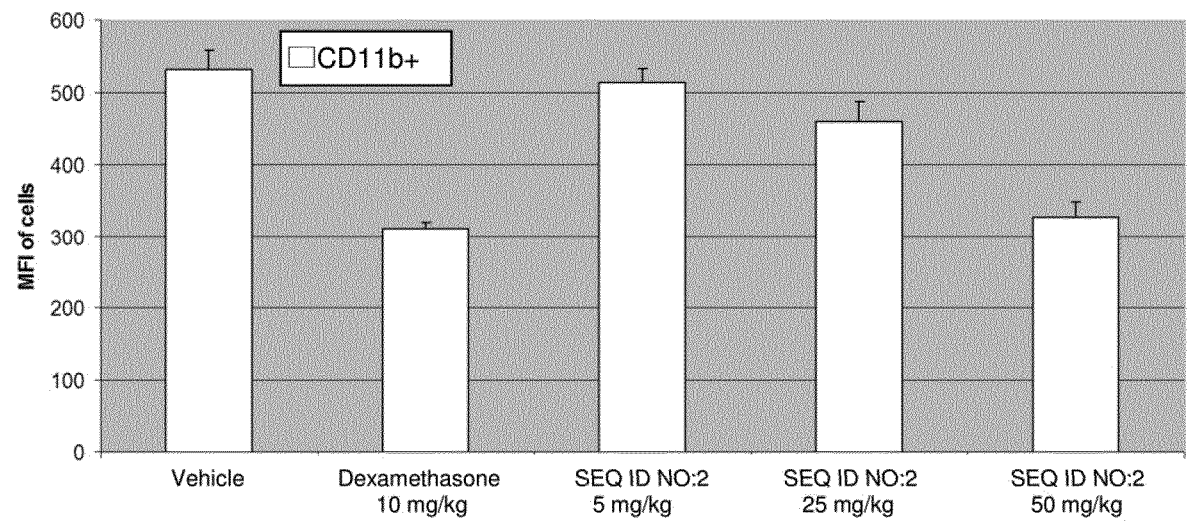

The proportion of CD11b+CD14+ cells and expression of CD11b in white blood cells are shown in FIG. 5. The dexamethasone group had significantly reduced expression of CD11b on CD11b+ cells compared to the vehicle group, but had a similar proportion of CD11b+CD14+ cells in white blood cells. The group dosed with SEQ ID NO:2 at 5 mg/kg had similar expression of CD11b and a similar proportion of CD11b+CD14+ cells in white blood cells compared to the vehicle group.

Groups dosed with SEQ ID NO:2 at 25 and 50 mg/kg had a significantly lower proportion of CD11b+CD14+ cells in blood white cells compared to the vehicle group. Similarly, these groups had lower expression of CD11b, with the difference being statistically significant for the group dosed at 50 mg/kg.

Collectively, results from the study indicate that SEQ ID NO:2 has anti-inflammatory properties in the LPS-induced cytokine production model.

Example 6: Effect of SEQ ID NO:2 Treatment on LPS-Induced Mortality in C57BL/6 Mice Material and Methods Mice In this study, female C57BL/6 mice of 10-12 weeks old (Taconic Biosciences) were used. Animals had free access to autoclaved and acidified drinking water. Animals were housed under standard laboratory conditions, air conditioned and filtered with adequate fresh air supply. Animals were kept in a climate controlled environment.

Compounds

Lipopolysaccharide (LPS) from *E. coli* (O111:B4) was diluted in PBS.

SEQ ID NO:2 was stored in powder form at 4° C. until use. Powder was added to saline and vortexed into solution to prepare SEQ ID NO:2 stock solution.

Treatment

Mice were treated as displayed in table 5. One group of 20 control mice did not receive lipopolysaccharide. For all other groups, LPS was injected intraperitoneally at 10 mg/kg. Mice were intravenously injected 15 minutes and 60 minutes after LPS administration with SEQ ID NO:2 at concentrations of 10, 25, 50 and 100 mg/kg. Except group 6, which was intravenously injected once at 15 minutes and once at 120 minutes after LPS administration.

Survival Assay

When high doses of LPS are administered, animals will suffer LPS-induced shock and mortality may be observed. For 72 hours after LPS injection, mice were checked for mortality several times each day. All surviving mice were euthanized at the end of the study (day 3).

Results and Discussion

Figure 6:
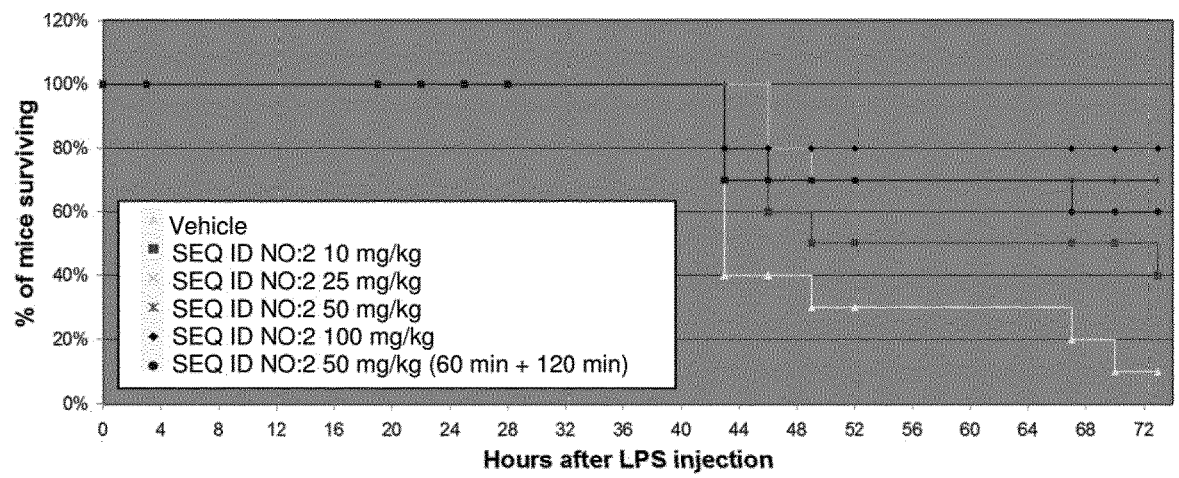
FIG. 6: Effects of treatment on survival rate after LPS injection in C57BL/6 mice. Female C57BL/6 mice were twice injected intravenously with SEQ ID NO:2 at 10, 25, 50 and 100 mg/kg. First injection took place 15 minutes after LPS administration, the second 1 hour after LPS injection. The $6^{th}$ group received two injections at 60 minutes and 2 hour after LPS administration. Survival incidence has been determined 72 hours after LPS injection (A). The percentages survival rate was plotted per 4 hours in (B) (n=20 mice per group); survival rate has been analysed using standard Mantel-Cox log-rank test.

As shown in in FIG. 6A and in the corresponding survival graph (FIG. 6B), SEQ ID NO:2 administered at 25, 50 and 100 mg/kg significantly improved survival compared to the vehicle treated mice. These findings suggest that intravenous administration of SEQ ID NO:2 is effective in treating LPS-induced shock in this study.

Example 7: Effect of SEQ ID NO:2 Treatment on Expanded Toxicology Analysis of Serum LPS-Induced Mortality in C57BL/6 Mice Materials and Methods Mice In this study, female C57BL/6 mice of 10-12 weeks old (Taconic Biosciences) were used. Animals had free access to autoclaved and acidified drinking water. Animals were housed under standard laboratory conditions, air conditioned and filtered with adequate fresh air supply. Animals were kept in a climate-controlled environment.

Compounds

Lipopolysaccharide (LPS) from *E. coli* (O111:B4) was diluted in PBS. SEQ ID NO:2 was stored in powder form at 4° C. until use. Powder was added to saline and vortexed into solution to prepare SEQ ID NO:2 stock solution.

Treatment

Mice were treated as displayed in table 6. One group of 20 control mice did not receive lipopolysaccharide. For all other groups, LPS was injected intraperitoneally at 10 mg/kg. Mice were intravenously injected 15 minutes and 60 minutes after LPS administration with SEQ ID NO:2 at concentrations of 10, 25, 50 and 100 mg/kg. Except group 7, which was intravenously injected once at 15 minutes and once at 120 minutes after LPS administration.

TABLE 5

Treatment regimen

| Group | Treatment | Dose | Route | Time of administration | Volume | Purpose |
|---|---|---|---|---|---|---|
| 1 | Vehicle | — | i.v. | Minute 15<br>Minute 60 | 10 mL/kg | Negative control for treatment |
| 2 | SEQ ID NO: 2 | 10 mg/kg | i.v. | Minute 15<br>Minute 60 | 10 mL/kg | Test |
| 3 | SEQ ID NO: 2 | 25 mg/kg | i.v. | Minute 15<br>Minute 60 | 10 mL/kg | Test |
| 4 | SEQ ID NO: 2 | 50 mg/kg | i.v. | Minute 15<br>Minute 60 | 10 mL/kg | Test |
| 5 | SEQ ID NO: 2 | 100 mg/kg | i.v. | Minute 15<br>Minute 60 | 10 mL/kg | Test |
| 6 | SEQ ID NO: 2 | 50 mg/kg | i.v. | Minute 60<br>Minute 120 | 10 mL/kg | Test |

TABLE 6

Treatment regimen

| Group | Treatment | Dose | Route | Time of administration | Volume | Purpose |
|---|---|---|---|---|---|---|
| 1 | Vehicle No LPS | — | i.v. | Minute 15 Minute 60 | 10 mL/kg | Normal control |
| 2 | Vehicle | — | i.v. | Minute 15 Minute 60 | 10 mL/kg | Negative control for treatment |
| 3 | SEQ ID NO: 2 | 10 mg/kg | i.v. | Minute 15 Minute 60 | 10 mL/kg | Test |
| 4 | SEQ ID NO: 2 | 25 mg/kg | i.v. | Minute 15 Minute 60 | 10 mL/kg | Test |
| 5 | SEQ ID NO: 2 | 50 mg/kg | i.v. | Minute 15 Minute 60 | 10 mL/kg | Test |
| 6 | SEQ ID NO: 2 | 100 mg/kg | i.v. | Minute 15 Minute 60 | 10 mL/kg | Test |
| 7 | SEQ ID NO: 2 | 50 mg/kg | i.v. | Minute 60 Minute 120 | 10 mL/kg | Test |

Blood Collection and Analysis

Blood collected at Hour 28 was analyzed for expanded toxicology panel performed by IDEXX Laboratories, Inc. (N. Grafton, Mass.). We attempted to collect enough blood to run each analysis 5 times for each group.

Extended Toxicology Panel

The extended toxicology analysis measured concentrations of AST, ALT, creatine kinase, albumin, total protein, BUN, cholesterol, glucose, phosphorus, triglycerides, HDL cholesterol, bile acid, LDL cholesterol, total bilirubin, GGT, bilirubin conjugated, and creatinine. Here, results are shown for AST, ALT, creatine kinase, albumin, total protein, BUN, cholesterol, phosphorus, triglycerides, cholesterol, and creatinine.

Results and Discussion

Figure 7:
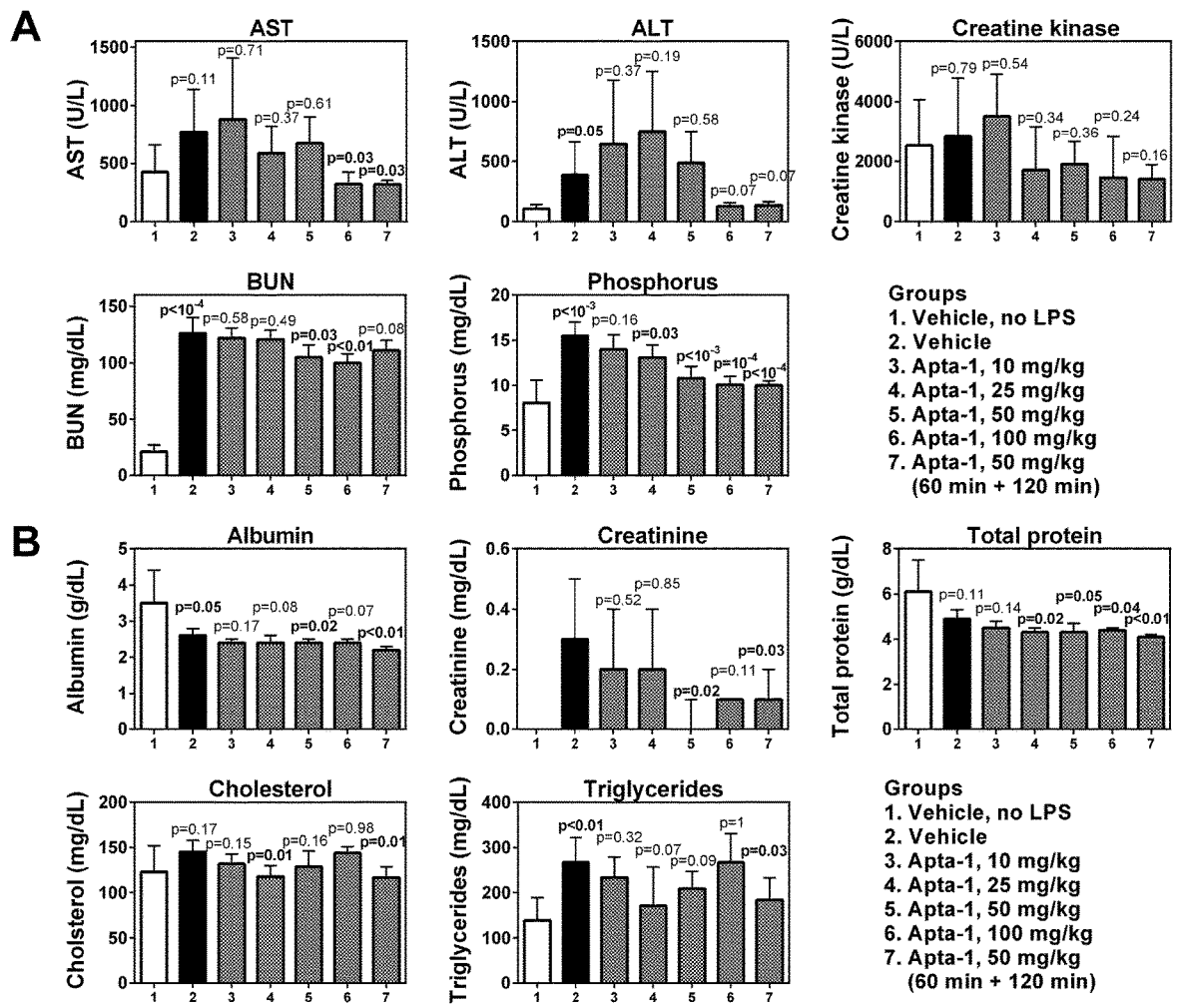
FIG. 7: Effect of SEQ ID NO:2 treatment on expanded toxicology analysis of serum LPS-induced mortality in C57BL/6 mice. Female C57BL/6 mice were twice injected intravenously with SEQ ID NO:2 at 10, 25, 50 and 100 mg/kg. First injection took place 15 minutes after LPS administration, the second 1 hour after LPS injection. The $7^{th}$ group received two injections at 60 minutes and 2 hour after LPS administration. (A) Serum concentrations of AST, ALT, creatine kinase, BUN and phosphorus in each group. Blood was collected after 28 hours. (B) Serum concentrations of albumin, creatinine, total protein, cholesterol and triglycerides in each group. Blood was collected after 28 hours. P-values were calculated by t-test. P-values of group 2 (vehicle) are given relative to group 1 (vehicle, no LPS). P-values of all other groups are determined relative to group 2 (vehicle).

FIG. 7A shows the concentrations for AST, ALT, creatine kinase, BUN, and phosphorus. These were the analytes that showed significant improvements in previous Hooke study 20170510-2 (Aptahem study APT1-17-PPD018), and also showed improvements in this study, although the improvements in ALT and creatine kinase did not reach statistical significance.

FIG. 7B shows the concentrations for albumin, creatinine, total protein, cholesterol and triglycerides. Triglycerides showed significant improvements in 50 mg/kg SEQ ID NO:2 administered at 60 and 120 min after LPS administration. Creatinine showed significant improvements in 50 mg/kg SEQ ID NO:2 administered at the time schedule 15 and 60 min as well as for time schedule 60 and 120 min after LPS administration, respectively. Cholesterol showed significant improvements in 25 mg/kg SEQ ID NO:2 and in 50 mg/kg SEQ ID NO:2 administered at the time schedule 15 and 60 min.

Overall, serum concentrations of AST, creatinine, BUN, phosphorus, cholesterol and triglycerides were significantly improved (with levels more similar to naive healthy mice) in the groups treated intravenously with SEQ ID NO:2, compared to the vehicle treated group.

These findings suggest that intravenous administration of SEQ ID NO:2 is effective in protecting against organ damage or failure, particularly liver and/or kidney damage or failure, during LPS-induced shock.

Example 8: Effect of SEQ ID NO:2 Treatment on Fibrinogen and D-Dimer Analysis of Serum LPS-Induced Mortality in C57BL/6 Mice Material and Methods Mice In this study, female C57BL/6 mice of 10-12 weeks old (Taconic Biosciences) were used. Animals had free access to autoclaved and acidified drinking water. Animals were housed under standard laboratory conditions, air conditioned and filtered with adequate fresh air supply. Animals were kept in a climate-controlled environment.

Compounds

Lipopolysaccharide (LPS) from E. coli (O111:B4) was diluted in PBS. SEQ ID NO:2 was stored in powder form at 4° C. until use. Powder was added to saline and vortexed into solution to prepare SEQ ID NO:2 stock solution.

Treatment

Mice were treated as displayed in table 7. One group of 20 control mice did not receive lipopolysaccharide. For all other groups, LPS was injected intraperitoneally at 10 mg/kg. Mice were intravenously injected 15 minutes and 60 minutes after LPS administration with SEQ ID NO:2 at concentrations of 10, 25, 50 and 100 mg/kg. Except group 7, which was intravenously injected once at 15 minutes and once at 120 minutes after LPS administration.

TABLE 7

Treatment regimen

| Group | Treatment | Dose | Route | Time of administration | Volume | Purpose |
|---|---|---|---|---|---|---|
| 1 | Vehicle/No LPS | — | i.v. | Minute 15 Minute 60 | 10 mL/kg | Normal control |
| 2 | Vehicle | — | i.v. | Minute 15 Minute 60 | 10 mL/kg | Negative control for treatment |
| 3 | SEQ ID NO: 2 | 10 mg/kg | i.v. | Minute 15 Minute 60 | 10 mL/kg | Test |

TABLE 7-continued

Treatment regimen

| Group | Treatment | Dose | Route | Time of administration | Volume | Purpose |
|---|---|---|---|---|---|---|
| 4 | SEQ ID NO: 2 | 25 mg/kg | i.v. | Minute 15<br>Minute 60 | 10 mL/kg | Test |
| 5 | SEQ ID NO: 2 | 50 mg/kg | i.v. | Minute 15<br>Minute 60 | 10 mL/kg | Test |
| 6 | SEQ ID NO: 2 | 100 mg/kg | i.v. | Minute 15<br>Minute 60 | 10 mL/kg | Test |
| 7 | SEQ ID NO: 2 | 50 mg/kg | i.v. | Minute 60<br>Minute 120 | 10 mL/kg | Test |

Blood Collection and Analysis

Blood collected at Hour 28 was analysed for fibrinogen and D-dimer analysis from citrated plasma performed by IDEXX Laboratories, Inc. (N. Grafton, Mass.). Hook Laboratories attempted to collect enough blood to run each analysis 5 times for each group, but in one case (citrated plasma for D-dimer, for Group 4) we were able to collect only enough blood to run the analysis 4 times.

Results and Discussion

Figure 8:
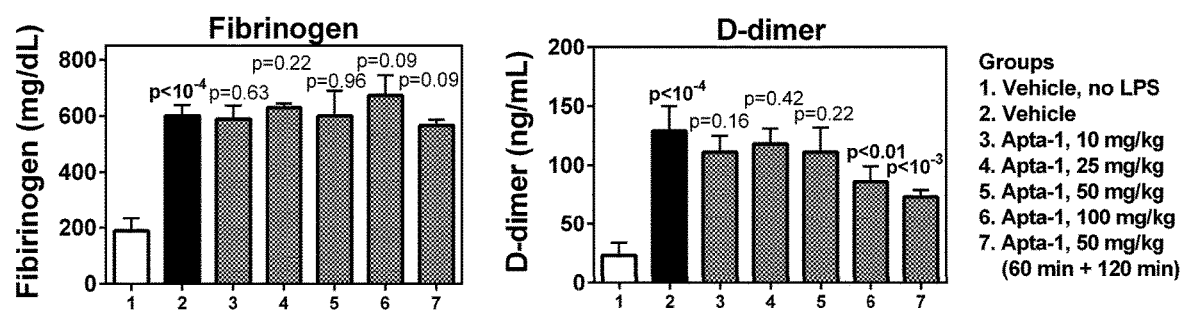
FIG. 8: Effect of SEQ ID NO:2 treatment on fibrinogen and D-dimer analysis of serum LPS-induced mortality in C57BL/6 mice. Female C57BL/6 mice were twice injected intravenously with SEQ ID NO:2 at 10, 25, 50 and 100 mg/kg. First injection took place 15 minutes after LPS administration, the second 1 hour after LPS injection. The $7^{th}$ group received two injections at 60 minutes and 2 hour after LPS administration. Serum levels of fibrinogen and D-dimer are shown. Blood was collected after 28 hours. P-values were calculated by t-test. P-values of group 2 (vehicle) are given relative to group 1 (vehicle, no LPS). P-values of all other groups are determined relative to group 2 (vehicle).

FIG. 8 shows the concentrations for fibrinogen and D-dimers. There were no significant differences in fibrinogen concentrations in plasma between SEQ ID NO:2 treated mice and the vehicle treated mice. Plasma D-dimer concentrations were significantly lower in the 100 mg/kg SEQ ID NO:2 treated group and the group treated with 50 mg/kg SEQ ID NO:2 at 60 and 120 minutes compared to the vehicle treated group.

Thus, Apta-1 treatment reduced D-dimer in a dose dependent manner with the greatest reductions observed in plasma of the Apta-1 group treated at 60 and 120 minutes after LPS dosing.

The above findings suggest that intravenous administration of SEQ ID NO:2 significantly suppresses D-dimers, a marker linked with coagulation, and a marker of poor outcome in various critical conditions in LPS-induced shock.

LIST OF REFERENCES

Clowes G H., Jr "Survival or death from sepsis." Surgery 67 (1970): 374-382.

Gando S, Saitoh D, Ogura H, Mayumi T, Koseki K, Ikeda T, Ishikura H, Iba T, Ueyama M, Eguchi Y, Ohtomo Y, Okamoto K, Kushimoto S, Endo S, Shimazaki S, "Japanese Association for Acute Medicine Disseminated Intravascular Coagulation (JAAM DIC) Study Group: Natural history of disseminated intravascular coagulation diagnosed based on the newly established diagnostic criteria for critically ill patients: results of a multicenter, prospective survey." Crit Care Med 36 (2008): 145-150.

Hasegawa H et al, Methods for Improving Aptamer Binding Affinity, Molecules 2016, 21(4), 421.

Lei M G, Gao J J, Morrison D C, Qureshi N. "Pathogenesis of sepsis: current concepts and emerging therapies. Mo Med 100 (2003): 524-529.

Parrillo J E, Parker M M, Natanson C, et al. "Septic shock in humans: advances in the understanding of pathogenesis, cardiovascular dysfunction, and therapy." Ann Intern Med 113 (1990): 227-242.

Stupnisek M, Franjic S, Drmic D, Hrelec M, Kolenc D, Radic B, et al. (2012) Pentadecapeptide BPC 157 reduces bleeding time and thrombocytopenia after amputation in rats treated with heparin, warfarin or aspirin. Thromb Res 129: 652-659

Lee J J, Jin Y R, Yu J Y, Munkhtsetseg T, Park E S, Lim Y, Kim T J, Pyo M Y, Hong J T, Yoo H S. et al. Antithrombotic and antiplatelet activities of fenofibrate, a lipid-lowering drug. Atherosclerosis. 2009; 206(2):375-382.

The invention claimed is:

1. A method for alleviating one or more symptom(s) and/or characteristic(s) and/or for improving a parameter of a disease or condition wherein inflammation and/or coagulation and/or organ damage or failure occur in an individual, the method comprising administering to said individual an effective amount of a nucleic acid molecule, said nucleic acid molecule comprising the nucleotide sequence set forth as SEQ ID NO:1 or a nucleotide sequence at least 95% identical thereto or comprising the nucleotide sequence set forth as SEQ ID NO:2 or nucleotide sequence at least 95% identical thereto or a pharmaceutical composition comprising said nucleic acid molecule and a pharmaceutically acceptable carrier, adjuvant, salt, diluent and/or excipient.

2. The method according to claim 1, wherein the disease or condition wherein inflammation and/or coagulation and/or organ damage or failure occur is selected from acute coronary syndrome (ACS), thrombosis, peripheral vessel obstruction, obstructive arteriosclerosis, vasculitis, functional disorder occurring after heart surgery, complication caused by organ transplantation, angina pectoris, transient ischemic attack, toxemia of pregnancy (preeclampsia, eclampsia), diabetes, liver veno-occlusive disease (VOD), deep venous thrombosis (DVT), sepsis, septic shock, severe sepsis, trauma, acute respiratory distress syndrome (ARDS), disseminated intravascular coagulation (DIC), rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, non-alcoholic steatosis, sarcoidosis, autoimmune diabetes, diabetes mellitus, uveitis, multiple sclerosis, Controlling Allograft Rejection after organ transplantation, graft versus host disease (GVHD), inflammatory lung diseases including asthma and chronic obstructive pulmonary disease (COPD), systemic lupus erythematosus (SLE), sarcoidosis, atopic dermatitis, cancer, infection, poisoning, aspiration syndromes, hypoperfusion or shock, heat-induced illness, ischemia, ischemia-reperfusion injury (IRI), autoimmune disease, hemorrhage, pancreatitis, bacteremia, burns, systemic inflammatory response syndrome (SIRS) and multiple organ failure or multiple organ dysfunction syndrome, or a complication or an effect of the progression that is linked to one of these diseases or conditions.

3. The method according to claim 1, wherein said nucleic acid molecule comprises the nucleotide sequence set forth as SEQ ID NO:1 or comprises the nucleotide sequence set forth as SEQ ID NO:2.

4. The method according to claim 1, whereby
(a) a parameter associated with inflammation such as the level of a pro-inflammatory cytokine, the level of a pro-inflammatory integrin and/or the number of pro-inflammatory infiltrates is decreased and/or
(b) a parameter associated with coagulation such as fibrin clot formation and/or thrombin concentration is decreased and/or
(c) a parameter associated with organ damage or failure such as AST, ALT, GGT, ALP, LDH, creatine kinase, BUN, albumin, creatinine, glucose, bile acid, total bilirubin, conjugated bilirubin, phosphorus, total protein, LDL cholesterol, HDL cholesterol, cholesterol and/or triglycerides is improved.

5. The method according to claim 1, wherein the nucleic acid molecule is single stranded and/or a nucleotide of this nucleic acid molecule is modified compared to a nucleotide present in RNA.

6. The method according to claim 5, wherein a pyrimidine of the nucleic acid molecule is fluorinated.

7. The method according to claim 6, wherein all pyrimidines of the nucleic acid molecule are fluorinated.

8. The method according to claim 1, wherein the individual is administered a pharmaceutical composition comprising said nucleic acid molecule.

9. The method according to claim 1, wherein the nucleic acid molecule or pharmaceutical comprising the nucleic acid molecule is intravenously administered to the individual.

10. A method for preventing, treating, regressing, curing and/or delaying a disease or a condition wherein inflammation and/or coagulation and/or organ damage or failure occurs the method comprising administering to an individual in need thereof an effective amount of a nucleic acid molecule, said nucleic acid molecule comprising the nucleotide sequence set forth as SEQ ID NO:1 or a nucleotide sequence at least 95% identical thereto or comprising the nucleotide sequence set forth as SEQ ID NO:2 or nucleotide sequence at least 95% identical thereto or a pharmaceutical composition comprising an effective amount of said nucleic acid molecule.

11. The method according to claim 10, wherein said nucleic acid molecule comprises the nucleotide sequence set forth as SEQ ID NO:1 or comprises the nucleotide sequence set forth as SEQ ID NO:2.

12. The method according to claim 10, wherein the disease or condition wherein inflammation and/or coagulation and/or organ damage or failure occur is selected from acute coronary syndrome (ACS), thrombosis, peripheral vessel obstruction, obstructive arteriosclerosis, vasculitis, functional disorder occurring after heart surgery, complication caused by organ transplantation, angina pectoris, transient ischemic attack, toxemia of pregnancy (preeclampsia, eclampsia), diabetes, liver veno-occlusive disease (VOD), deep venous thrombosis (DVT), sepsis, septic shock, severe sepsis, trauma, acute respiratory distress syndrome (ARDS), disseminated intravascular coagulation (DIC), rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, non-alcoholic steatosis, sarcoidosis, autoimmune diabetes, diabetes mellitus, uveitis, multiple sclerosis, Controlling Allograft Rejection after organ transplantation, graft versus host disease (GVHD), inflammatory lung diseases including asthma and chronic obstructive pulmonary disease (COPD), systemic lupus erythematosus (SLE), sarcoidosis, atopic dermatitis, cancer, infection, poisoning, aspiration syndromes, hypoperfusion or shock, heat-induced illness, ischemia, ischemia-reperfusion injury (IRI), autoimmune disease, hemorrhage, pancreatitis, bacteremia, burns, systemic inflammatory response syndrome (SIRS) and multiple organ failure or multiple organ dysfunction syndrome, or a complication or an effect of the progression that is linked to one of these diseases or conditions.

13. The method according to claim 10, wherein the nucleic acid molecule or pharmaceutical comprising the nucleic acid molecule is intravenously administered to the individual.

14. A method for inhibiting and/or preventing coagulation of the blood in a subject in need thereof, comprising administering to the subject an effective amount of a nucleic acid molecule, said nucleic acid molecule comprising the nucleotide sequence set forth as SEQ ID NO:1 or a nucleotide sequence at least 95% identical thereto or comprising the nucleotide sequence set forth as SEQ ID NO:2 or nucleotide sequence at least 95% identical thereto or a pharmaceutical composition comprising said nucleic acid molecule and a pharmaceutically acceptable carrier, adjuvant, salt, diluent and/or excipient.

15. The method according to claim 14, wherein the nucleic acid molecule comprises the nucleotide sequence set forth as SEQ ID NO:2 or a nucleotide sequence at least 95% identical thereto.

16. The method according to claim 14, wherein the individual in need thereof is an individual with sepsis.

17. The method according to claim 14, wherein the nucleic acid molecule or composition comprising the nucleic acid molecule is administered intravenously to the individual.

* * * * *

SEQUENCE LISTING

```
<160> NUMBER OF SEQ ID NOS: 2

<210> SEQ ID NO 1
<211> LENGTH: 90
<212> TYPE: RNA
<213> ORGANISM: Artificial Sequence
<220> FEATURE:
<223> OTHER INFORMATION: Synthesized

<400> SEQUENCE: 1
gggaauucga gcucgguacc aacaauacga cuacaccauc aaaaguauua ucuugcaucg      60
aagguuggca cguagcaagc ucugcagucg                                      90

<210> SEQ ID NO 2
<211> LENGTH: 90
<212> TYPE: RNA
<213> ORGANISM: Artificial Sequence
<220> FEATURE:
<223> OTHER INFORMATION: Synthesized
```

```
-continued

<220> FEATURE:
<221> NAME/KEY: misc_feature
<222> LOCATION: (6)..(7)
<223> OTHER INFORMATION: uracil is fluorinated
<220> FEATURE:
<221> NAME/KEY: misc_feature
<222> LOCATION: (8)..(8)
<223> OTHER INFORMATION: cytosine is fluorinated
<220> FEATURE:
<221> NAME/KEY: misc_feature
<222> LOCATION: (12)..(12)
<223> OTHER INFORMATION: cytosine is fluorinated
<220> FEATURE:
<221> NAME/KEY: misc_feature
<222> LOCATION: (13)..(13)
<223> OTHER INFORMATION: uracil is fluorinated
<220> FEATURE:
<221> NAME/KEY: misc_feature
<222> LOCATION: (14)..(14)
<223> OTHER INFORMATION: cytosine is fluorinated
<220> FEATURE:
<221> NAME/KEY: misc_feature
<222> LOCATION: (17)..(17)
<223> OTHER INFORMATION: uracil is fluorinated
<220> FEATURE:
<221> NAME/KEY: misc_feature
<222> LOCATION: (19)..(20)
<223> OTHER INFORMATION: cytosine is fluorinated
<220> FEATURE:
<221> NAME/KEY: misc_feature
<222> LOCATION: (23)..(23)
<223> OTHER INFORMATION: cytosine is fluorinated
<220> FEATURE:
<221> NAME/KEY: misc_feature
<222> LOCATION: (26)..(26)
<223> OTHER INFORMATION: uracil is fluorinated
<220> FEATURE:
<221> NAME/KEY: misc_feature
<222> LOCATION: (28)..(28)
<223> OTHER INFORMATION: cytosine is fluorinated
<220> FEATURE:
<221> NAME/KEY: misc_feature
<222> LOCATION: (31)..(31)
<223> OTHER INFORMATION: cytosine is fluorinated
<220> FEATURE:
<221> NAME/KEY: misc_feature
<222> LOCATION: (32)..(32)
<223> OTHER INFORMATION: uracil is fluorinated
<220> FEATURE:
<221> NAME/KEY: misc_feature
<222> LOCATION: (34)..(34)
<223> OTHER INFORMATION: cytosine is fluorinated
<220> FEATURE:
<221> NAME/KEY: misc_feature
<222> LOCATION: (36)..(37)
<223> OTHER INFORMATION: cytosine is fluorinated
<220> FEATURE:
<221> NAME/KEY: misc_feature
<222> LOCATION: (39)..(39)
<223> OTHER INFORMATION: uracil is fluorinated
<220> FEATURE:
<221> NAME/KEY: misc_feature
<222> LOCATION: (40)..(40)
<223> OTHER INFORMATION: cytosine is fluorinated
<220> FEATURE:
<221> NAME/KEY: misc_feature
<222> LOCATION: (46)..(46)
<223> OTHER INFORMATION: uracil is fluorinated
<220> FEATURE:
<221> NAME/KEY: misc_feature
<222> LOCATION: (48)..(49)
<223> OTHER INFORMATION: uracil is fluorinated
<220> FEATURE:
<221> NAME/KEY: misc_feature
<222> LOCATION: (51)..(51)
<223> OTHER INFORMATION: uracil is fluorinated
<220> FEATURE:
<221> NAME/KEY: misc_feature
<222> LOCATION: (52)..(52)
```

```
<223> OTHER INFORMATION: cytosine is fluorinated
<220> FEATURE:
<221> NAME/KEY: misc_feature
<222> LOCATION: (53)..(54)
<223> OTHER INFORMATION: uracil is fluorinated
<220> FEATURE:
<221> NAME/KEY: misc_feature
<222> LOCATION: (56)..(56)
<223> OTHER INFORMATION: cytosine is fluorinated
<220> FEATURE:
<221> NAME/KEY: misc_feature
<222> LOCATION: (58)..(58)
<223> OTHER INFORMATION: uracil is fluorinated
<220> FEATURE:
<221> NAME/KEY: misc_feature
<222> LOCATION: (59)..(59)
<223> OTHER INFORMATION: cytosine is fluorinated
<220> FEATURE:
<221> NAME/KEY: misc_feature
<222> LOCATION: (65)..(66)
<223> OTHER INFORMATION: uracil is fluorinated
<220> FEATURE:
<221> NAME/KEY: misc_feature
<222> LOCATION: (69)..(69)
<223> OTHER INFORMATION: cytosine is fluorinated
<220> FEATURE:
<221> NAME/KEY: misc_feature
<222> LOCATION: (71)..(71)
<223> OTHER INFORMATION: cytosine is fluorinated
<220> FEATURE:
<221> NAME/KEY: misc_feature
<222> LOCATION: (73)..(73)
<223> OTHER INFORMATION: uracil is fluorinated
<220> FEATURE:
<221> NAME/KEY: misc_feature
<222> LOCATION: (76)..(76)
<223> OTHER INFORMATION: cytosine is fluorinated
<220> FEATURE:
<221> NAME/KEY: misc_feature
<222> LOCATION: (80)..(80)
<223> OTHER INFORMATION: cytosine is fluorinated
<220> FEATURE:
<221> NAME/KEY: misc_feature
<222> LOCATION: (81)..(81)
<223> OTHER INFORMATION: uracil is fluorinated
<220> FEATURE:
<221> NAME/KEY: misc_feature
<222> LOCATION: (82)..(82)
<223> OTHER INFORMATION: cytosine is fluorinated
<220> FEATURE:
<221> NAME/KEY: misc_feature
<222> LOCATION: (83)..(83)
<223> OTHER INFORMATION: uracil is fluorinated
<220> FEATURE:
<221> NAME/KEY: misc_feature
<222> LOCATION: (85)..(85)
<223> OTHER INFORMATION: cytosine is fluorinated
<220> FEATURE:
<221> NAME/KEY: misc_feature
<222> LOCATION: (88)..(88)
<223> OTHER INFORMATION: uracil is fluorinated
<220> FEATURE:
<221> NAME/KEY: misc_feature
<222> LOCATION: (89)..(89)
<223> OTHER INFORMATION: cytosine is fluorinated

<400> SEQUENCE: 2
gggaauucga gcucgguacc aacaauacga cuacaccauc aaaaguauua ucuugcaucg      60
aagguuggca cguagcaagc ucugcagucg                                      90
```